United States Patent
Zhu et al.

(10) Patent No.: US 10,329,277 B2
(45) Date of Patent: Jun. 25, 2019

(54) N-(2-((2-(DIMETHYLAMINO)ETHYL)(METHYL)AMINO)-4-METHOXY-5-((4-(3-METHYL-2-OXO-2,3-DIHYDRO-1H-BENZO[D]IMIDAZOL-1-YL)PYRIMIDIN-2-YL)AMINO)PHENYL)ACRYLAMIDE HYDROCHLORIDE AS AN INHIBITOR OF EPIDERMAL GROWTH FACTOR RECEPTOR ACTIVITY

(71) Applicants: CHIA TAI TIANQING PHARMACEUTICAL GROUP CO., LTD., Lianyungang (CN); LIANYUNGANG RUNZHONG PHARMACEUTICAL CO., LTD., Lianyungang (CN); Centaurus Biopharma Co., Ltd., Beijing (CN)

(72) Inventors: Yan Zhu, Beijing (CN); Na Zhao, Beijing (CN); Xianxing Shang, Beijing (CN); Yuandong Hu, Beijing (CN); Yong Peng, Beijing (CN); Hui Zhang, Beijing (CN); Bo Liu, Beijing (CN); Hong Luo, Beijing (CN); Yongxin Han, Beijing (CN); Ling Yang, Lianyungang (CN); Hongjiang Xu, Lianyungang (CN)

(73) Assignees: CHIA TAI TIANQING PHARMACEUTICAL GROUP CO., LTD., Lianyungang, Jiangsu (CN); LIANYUNGANG RUNZHONG PHARMACEUTICAL CO., LTD., Lianyungang, Jiangsu (CN); CENTAURUS BIOPHARMA CO., LTD., Beijing (CN)

( * ) Notice: Subject to any disclaimer, the term of this patent is extended or adjusted under 35 U.S.C. 154(b) by 0 days.

(21) Appl. No.: 15/745,329

(22) PCT Filed: Jul. 15, 2016

(86) PCT No.: PCT/CN2016/090149
§ 371 (c)(1),
(2) Date: Jan. 16, 2018

(87) PCT Pub. No.: WO2017/008761
PCT Pub. Date: Jan. 19, 2017

(65) Prior Publication Data
US 2018/0208581 A1    Jul. 26, 2018

(30) Foreign Application Priority Data

Jul. 16, 2015   (CN) .......................... 2015 1 0419018

(51) Int. Cl.
C07D 403/02     (2006.01)
C07D 403/04     (2006.01)
A61K 31/506     (2006.01)
C07D 413/04     (2006.01)
A61P 35/00      (2006.01)
A61K 31/5377    (2006.01)

(52) U.S. Cl.
CPC .......... *C07D 403/04* (2013.01); *A61K 31/506* (2013.01); *A61K 31/5377* (2013.01); *A61P 35/00* (2018.01); *C07D 413/04* (2013.01)

(58) Field of Classification Search
CPC .................................................... C07D 403/02
USPC ....................................................... 544/331
See application file for complete search history.

(56) References Cited

FOREIGN PATENT DOCUMENTS

| CA | 2966376 | * | 5/2016 |
|----|---------|---|--------|
| CN | 103702990 A | | 4/2014 |
| CN | 105085489 A | | 11/2015 |
| EP | 3345900 A1 | | 7/2018 |
| WO | 01/25220 A1 | | 4/2001 |
| WO | 01/60816 A1 | | 8/2001 |
| WO | 2011140338 A1 | | 11/2011 |

OTHER PUBLICATIONS

Jordan, V. C. Nature Reviews: Drug Discovery, 2, 2003, 205.*
Hackam, et al. JAMA, 296(14), 2006, 1731-1732.*

* cited by examiner

*Primary Examiner* — Douglas M Willis
(74) *Attorney, Agent, or Firm* — Kilpatrick Townsend & Stockton LLP

(57) ABSTRACT

The present disclosure relates to aniline pyrimidine derivatives or pharmaceutically acceptable salts thereof as EGFR inhibitors, specifically relates to compounds represented by formula (I) or pharmaceutically acceptable salts, pharmaceutical compositions, the method and uses thereof for treating EGFR mediated diseases.

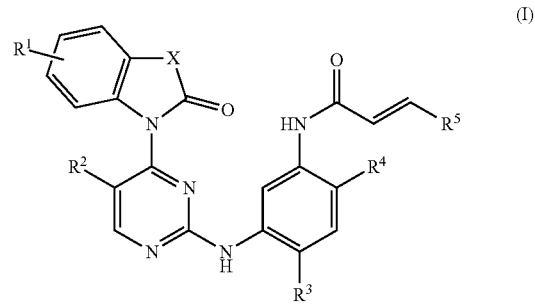

(I)

7 Claims, No Drawings

N-(2-((2-(DIMETHYLAMINO)ETHYL) (METHYL)AMINO)-4-METHOXY-5-((4-(3-METHYL-2-OXO-2,3-DIHYDRO-1H-BENZO[D]IMIDAZOL-1-YL)PYRIMIDIN-2-YL)AMINO)PHENYL)ACRYLAMIDE HYDROCHLORIDE AS AN INHIBITOR OF EPIDERMAL GROWTH FACTOR RECEPTOR ACTIVITY

CROSS-REFERENCE TO RELATED APPLICATION

The present application is a U.S. National Phase of PCT/CN2016/090149, filed Jul. 15, 2016 which claims the priority and benefit of Chinese Patent Application No. 201510419018.X filed on Jul. 16, 2015 before the State Intellectual Property Office of China, the disclosures of which is incorporated herein by reference in its entirety.

TECHNICAL FIELD

The present application relates to anilinopyrimidine derivatives as EGFR inhibitors, pharmaceutically acceptable salts thereof, and pharmaceutical compositions comprising the same, and methods or uses for treating EGFR-mediated diseases using the same.

BACKGROUND OF THE INVENTION

EGFR (Epidermal Growth Factor Receptor), also known as HER1 or ErbB1, is a receptor for cell proliferation and signal transduction of the epithelial growth factor (EGF). EGFR belongs to a member of the ErbB receptor family which includes EGFR (ErbB-1), HER2/c-neu (ErbB-2), HER3 (ErbB-3) and HER4 (ErbB-4). EGFR is a transmembrane glycoprotein with a molecular weight of 170 KDa, which belongs to a tyrosine kinase receptor.

EGFR is located on the surface of cell membranes and is activated by binding to ligands including EGF and TGFα. Upon being activated, EGFR undergoes a transition from a monomer to a dimer. The dimer includes not only the binding of two identical receptor molecules (homodimerization) but also the binding of different members of the human EGF-associated receptor (HER) tyrosine kinase family (heterodimerization). EGFR can activate its intracellular kinase pathways after dimerization, resulting in the phosphorylation of key tyrosine residues in the intracellular domain and the stimulation to many intracellular signaling pathways involved in cell proliferation and survival.

There exist high or abnormal expressions of EGFR in many solid tumors. EGFR is associated with tumor cell proliferation, angiogenesis, tumor invasion, metastasis and the inhibition of apoptosis. Possible mechanisms include the followings: enhanced downstream signal transduction caused by the high expressions of EGFR; the sustained activation of EGFR caused by the increased expressions of mutant EGFR receptors or ligands; the enhanced effect of autocrine loops; the destruction of receptor downregulation mechanisms; and the activation of aberrant signaling pathways, etc. Overexpressions of EGFR play an important role in the progression of malignant tumors. For example, overexpressions of EGFR have been found in gliocyte, kidney cancer, lung cancer, prostate cancer, pancreatic cancer, breast cancer and other tissues.

Aberrant expressions of EGFR and Erb-B2 play a crucial role in tumor transformation and growth. In the case of lung cancer, EGFR is expressed in 50% of non-small cell lung cancer (NSCLC) cases and its expression is associated with poor prognosis. The two factors allow EGFR and its family members to be major candidates of targeted therapy. Two types of small molecule inhibitors targeted to EGFR, gefitinib and erlotinib, were rapidly approved by the FDA of USA for the treatment of advanced NSCLC patients who have no response to traditional chemotherapy.

Early clinical data indicated that 10% of NSCLC patients have response to getifinib and erlotinib. Molecular biological analysis shows that in most cases, drug-responsive patients carry specific mutations in the EGFR-encoding genes: the deletion of amino acids at positions 747-750 in exon 19 accounts for 45% of mutations, and 10% of mutations occur in exons 18 and 20. The most common EGFR-activating mutations (L858R and delE746_A750) result in an increase in affinity for small molecule tyrosine kinase inhibitors (TKI) and a decrease in affinity for adenosine triphosphate (ATP) relative to wild type (WT) EGFR. T790M mutation is a point mutation in exon 20 of EGFR, which leads to acquired resistance to the treatment with gefitinib or erlotinib. A recent study shows that the combination of L858R and T790M mutations has a stronger affinity for ATP than L858R alone, and TKIs are ATP-competitive kinase inhibitors, and thereby resulting in a decreased binding rate between TKIs and kinase domains.

SUMMARY OF THE INVENTION

In one aspect, the present application provides a compound represented by Formula (I), or a pharmaceutically acceptable salt thereof:

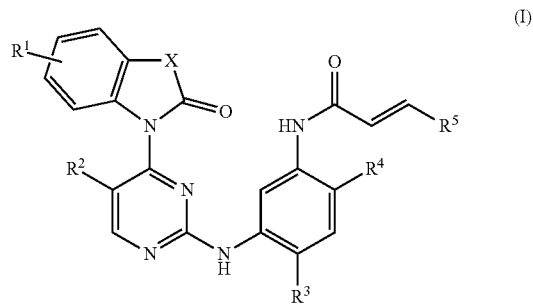

wherein:

X is selected from the group consisting of $NR^6$ and O;

$R^1$ and $R^2$ are independently selected from the group consisting of hydrogen, halo, $C_{1-4}$ alkyl and cyano;

$R^3$ is selected from the group consisting of $C_{1-4}$ alkyl and $C_{1-4}$ alkoxy;

$R^4$ is selected from the group consisting of [2-(dimethylamino)ethyl](methyl)amino, (2-hydroxyethyl)(methyl)amino and morpholin-4-yl;

$R^5$ is selected from the group consisting of hydrogen, $C_{1-4}$ alkyl and $C_{1-3}$ alkoxy$C_{1-3}$ alkyl;

$R^6$ is selected from the group consisting of hydrogen and $C_{1-4}$ alkyl.

In one embodiment of the present application, provided is a compound of Formula (I) or a pharmaceutically acceptable salt thereof, wherein:

X is selected from the group consisting of $NR^6$ and O;

$R^1$ and $R^2$ are independently selected from the group consisting of hydrogen, halo, and $C_{1-4}$ alkyl;

$R^3$ is $C_{1-4}$ alkoxy;

$R^4$ is selected from the group consisting of [2-(dimethylamino)ethyl](methyl)amino, (2-hydroxyethyl)(methyl)amino and morpholin-4-yl;

$R^5$ is selected from the group consisting of hydrogen, $C_{1-4}$ alkyl and $C_{1-3}$ alkoxy$C_{1-3}$ alkyl;

$R^6$ is selected from the group consisting of hydrogen and $C_{1-4}$ alkyl.

In one embodiment of the present application, provided is a compound of Formula (I) or a pharmaceutically acceptable salt thereof, wherein:

X is selected from the group consisting of $NR^6$ and O;

$R^1$ and $R^2$ are independently selected from the group consisting of hydrogen, chloro, bromo, fluoro and methyl;

$R^3$ is methoxy;

$R^4$ is selected from the group consisting of [2-(dimethylamino)ethyl](methyl)amino, (2-hydroxyethyl)(methyl)amino and morpholin-4-yl;

$R^5$ is selected from the group consisting of hydrogen and methoxymethyl;

$R^6$ is selected from the group consisting of hydrogen and methyl.

In one embodiment of the present application, the compounds of Formula (I) of the present application include the following compounds or pharmaceutically acceptable salts thereof:

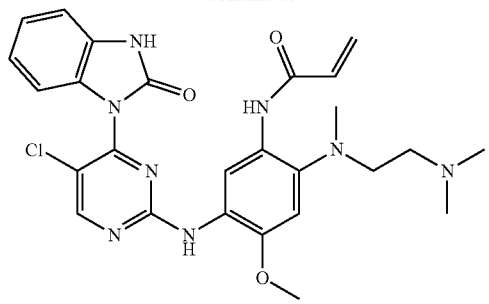

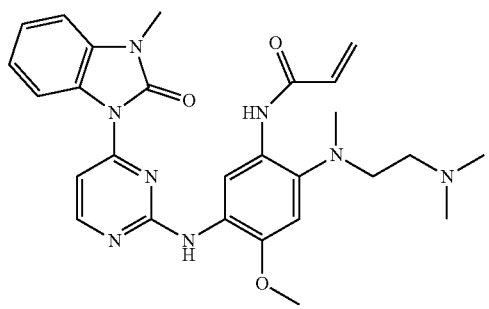

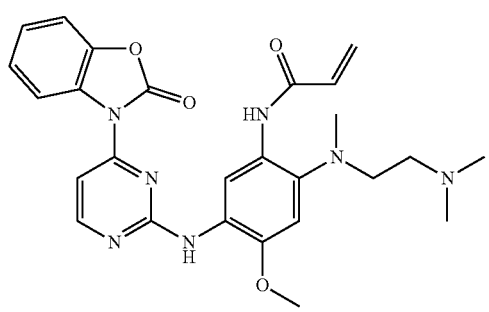

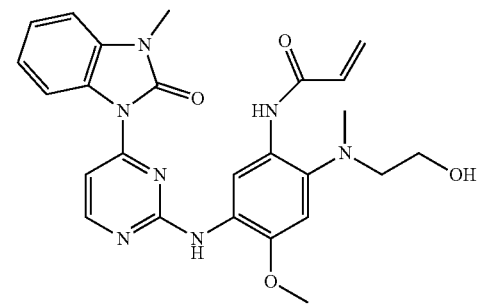

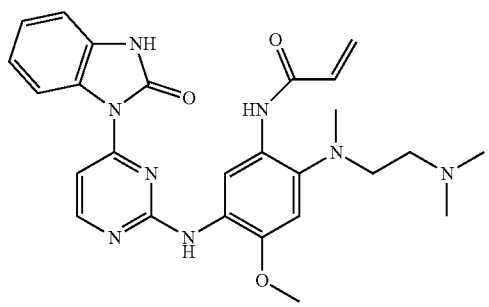

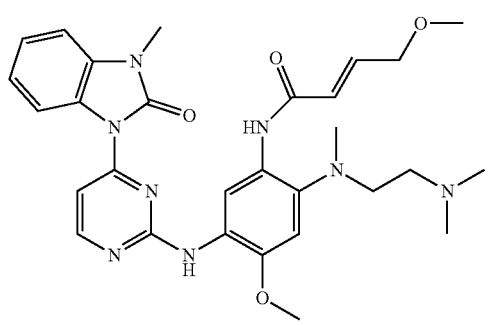

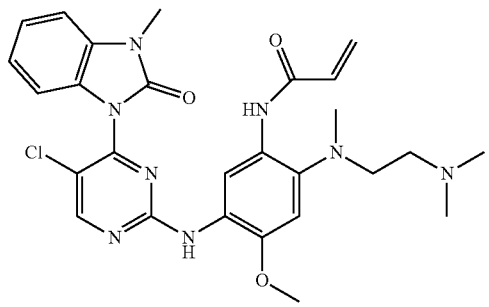

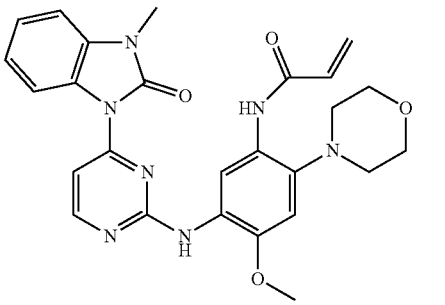

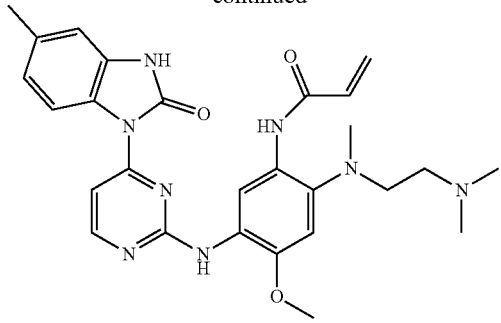

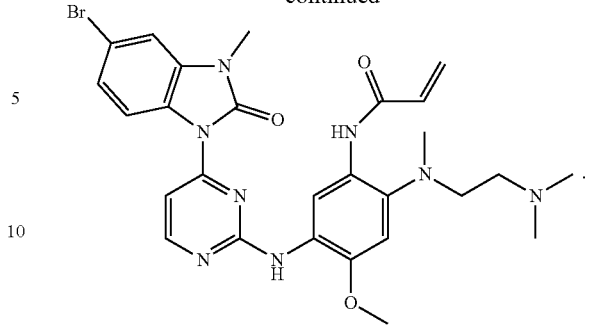

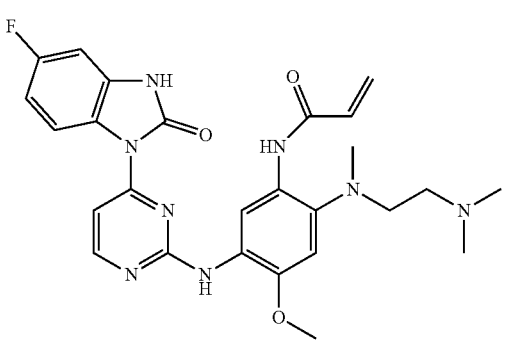

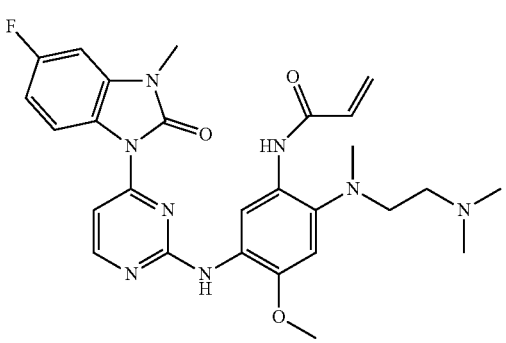

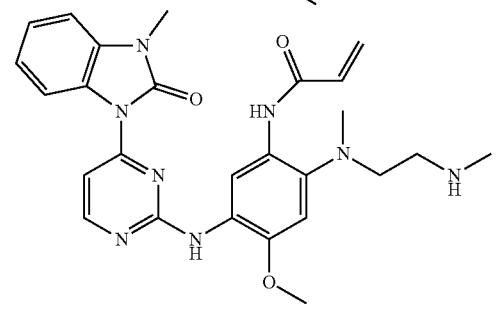

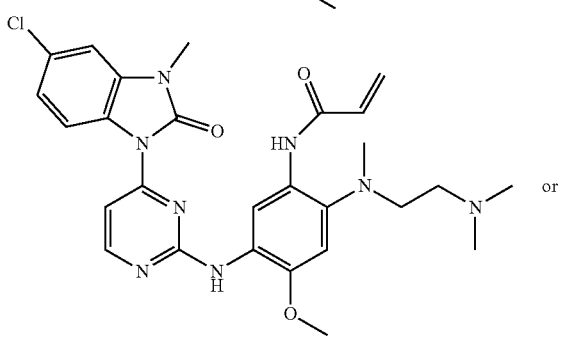

or

In another aspect, the present application provides a pharmaceutical composition comprising a compound represented by Formula (I) as disclosed herein or a pharmaceutically acceptable salt thereof, and one or more pharmaceutically acceptable carriers or excipients. Optionally, the pharmaceutical composition of the present application may further comprise one or more additional therapeutic agents.

In still another aspect, the present application provides a method for treating an EGFR-mediated disease, comprising administering to a subject in need thereof a compound of Formula (I) of the present application or a pharmaceutically acceptable salt thereof, or a pharmaceutical composition comprising the same.

In yet another aspect, the present application provides use of a compound of Formula (I) of the present application or a pharmaceutically acceptable salt thereof, or a pharmaceutical composition comprising the same, in the manufacture of a medicament for the treatment of an EGFR-mediated disease.

In some embodiments of the present application, the EGFR-mediated disease is selected from diseases mediated by an EGFR-L858R activating mutation.

In some embodiments of the present application, the EGFR-mediated disease is selected from diseases mediated by an EGFR-T790M activating mutation. In some embodiments, the EGFR-mediated disease is selected from diseases mediated by EGFR-L858R+EGFR-T790M double-activating mutations.

DETAILED DESCRIPTION OF THE INVENTION

Definitions

Unless stated otherwise, the terms and phrases used herein have the following meanings. A specific term or phrase shall not be considered as indefinite or unclear when it is not specifically defined, but should be understood according to the general meaning thereof. The trade names used herein refer to the corresponding products or the active ingredients thereof.

"$C_{m-n}$" as used herein means that the moiety has m-n carbon atoms. For example, "$C_{1-4}$ alkyl" means that the alkyl has 1-4 carbon atoms.

The numerical ranges as used herein refer to each integer within the given ranges. For example, "$C_{1-4}$" means that the group may have 1 carbon atom, 2 carbon atoms, 3 carbon atoms or 4 carbon atoms.

The term "halo" or "halogen" refers to fluoro, chloro, bromo, or iodo.

The term "cyano" refers to —CN group.

The term "alkyl" refers to a straight or branched saturated aliphatic hydrocarbon group consisting of carbon atoms and hydrogen atoms, which is attached to the rest of the molecule via a single bond. Non-limiting examples of alkyl include, but are not limited to, methyl, ethyl, propyl, 2-propyl, n-butyl, isobutyl or tert-butyl and the like.

The term "alkoxy" refers to an "—O-alkyl" group.

The term "pharmaceutically acceptable" refers to those compounds, materials, compositions and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

For example, a salt formed with an inorganic acid, a salt formed with an organic acid, a salt formed with an acidic amino acid, and the like can be mentioned as a pharmaceutically acceptable salt.

The pharmaceutically acceptable salt as used herein can be synthesized from a parent compound containing an acid radical or a base radical through a conventional chemical process. In general, the process for preparing such a salt comprises: reacting these compounds in the form of a free base with a stoichiometric appropriate acid in water or an organic solvent or a mixture of water and an organic solvent.

Some of the compounds of the present application may exist in a non-solvate form or a solvate form, including a hydrate form. In general, the solvate form is comparative to the non-solvate form, and both of them are contemplated by the present application. Some of the compounds of the present application may exist in a polymorphic or amorphous form.

Some of the compounds of the present application may have an unsymmetrical carbon atom (an optical center) or double bond. Racemates, diastereoisomers, geometrical isomers and individual isomers are all included within the scope of the present application.

The graphical representations for racemic, ambiscalemic and scalemic, or enantiomerically pure compounds herein are obtained from Maehr, J. Chem. Ed. 1985, 62: 114-120. Unless specified otherwise, the wedge shaped bond and dotted line bond are used to represent the absolute configuration of a stereoscopic center. Where the compounds herein contain an olefinic double bond or other geometrically unsymmetrical center, unless specified otherwise, they comprise E-, Z-geometrical isomers. Similarly, the tautomer forms are all included within the scope of the present application.

The compounds of the present application may have particular geometrical isomer or stereoisomer forms. Such compounds are all contemplated in the present application, including cis- and trans-isomers, (−)- and (+)-enantiomers, (R)- and (S)-enantiomers, diastereoisomers, (D)-isomers, (L)-isomers, and racemic mixtures thereof and other mixtures, such as a enantiomer or diastereoisomer-rich mixture. All such mixtures are included within the scope of the present application. Substituents such as alkyl may have additional unsymmetrical carbon atoms. Such isomers and mixtures thereof are all included within the scope of the present application.

Optically active (R)- and (S)-isomers and D- and L-isomers can be prepared by using chiral synthesis or chiral reagents, or other conventional technology. If one enantiomer of certain compound of the present application is desired, this enantiomer can be prepared by an asymmetric synthesis or a derivatization process with a chiral auxiliary, which comprises separating a mixture of diastereoisomers, and cleaving assistant groups to provide a desired pure enantiomer. Alternatively, when a molecule contains an alkaline functional group (such as amino) or an acidic functional group (such as carboxyl), a diastereoisomer salt can be formed by the molecule and an appropriate optically active acid or base, and then the diastereoisomer is resolved by a fractional crystallization or chromatography as well-known in the art, thereby recovering a pure enantiomer. In addition, the separation of an enantiomer and a diastereoisomer is generally achieved by a chromatography using a chiral stationary phase, or optionally combining with a chemical derivatization process (e.g., using an amine to produce a carbamate salt).

The compound of the present application may contain atomic isotopes at a non-natural ratio, on one or more atoms that constitute the compound. For example, atomic isotopes may be deuterium (D), tritium ($^3H$), iodine-125 ($^{125}I$) carbon-14 ($^{14}C$) and so on. The transformations formed by all the isotopes for the compound of the present application, whether they are radioactive or not, are all contemplated by the present application.

The term "pharmaceutically acceptable carrier" refers to those carriers which have no significant irritation to an organism and do not impair the bioactivity and property of the active compound. The "pharmaceutically acceptable carrier" refers to an inert substance which is administered with an active ingredient and is beneficial to the administration of the active ingredient, and includes but not limited to any of the following substances which are acceptable for use in humans or animals (e.g. livestocks) approved by the State Food and Drug Administration: glidants, sweetening agents, diluents, preservatives, dyes/colorants, flavoring agents, surfactants, wetting agents, dispersants, disintegrants, suspending agents, stabilizing agents, isotonic agents, solvents or emulsifying agents. Non-limiting examples of the carriers comprise calcium carbonate, calcium phosphate, various sugars and starches, cellulose derivatives, gelatines, vegetable oil and polyethylene glycol and the like. Other information regarding the carriers may refer to Remington: The Science and Practice of Pharmacy, 21st Ed., Lippincott, Williams & Wilkins (2005), of which the contents are incorporated herein by reference.

The term "excipient" generally refers to a carrier, diluent and/or medium used to formulate an effective pharmaceutical composition.

As for a pharmaceutical or pharmacological active agent, the term "effective amount" or "therapeutically effective amount" refers to the amount of a medicament or agent which is nontoxic but sufficient to achieve the desired effect. With respect to the oral formulation herein, the "effective amount" for an active substance in the composition refers to the amount required to achieve the desired effect in combination with another active substance in the composition. The determination of the effective amount varies from person to person and depends on the age and general condition of the receptor as well as the specific active substance. The effective amount in a specific case can be determined by a person skilled in the art through conventional tests.

The term "active ingredient", "therapeutic agent", "active substance" or "active agent" refers to a chemical entity which is useful for treating target disorders, diseases or conditions effectively.

The term "patient" or "subject" includes humans and animals, for example, mammals (such as primates, cattle, horses, pigs, dogs, cats, mice, rats, rabbits, goats, sheep and birds).

Specific Embodiments

In one aspect, the present application provides a compound represented by Formula (I), or a pharmaceutically acceptable salt thereof:

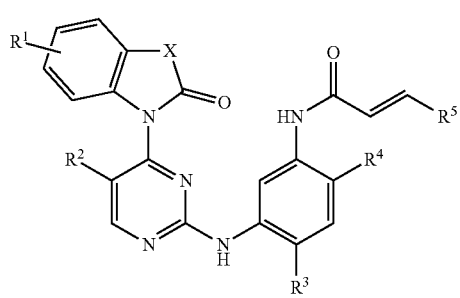
(I)

wherein:
X is selected from the group consisting of NR⁶ and O;
R¹ and R² are independently selected from the group consisting of hydrogen, halo, $C_{1-4}$ alkyl and cyano;
R³ is selected from the group consisting of $C_{1-4}$ alkyl and $C_{1-4}$ alkoxy;
R⁴ is selected from the group consisting of [2-(dimethylamino)ethyl](methyl)amino, (2-hydroxyethyl)(methyl)amino and morpholin-4-yl;
R⁵ is selected from the group consisting of hydrogen, $C_{1-4}$ alkyl and $C_{1-3}$ alkoxy$C_{1-3}$ alkyl;
R⁶ is selected from the group consisting of hydrogen and $C_{1-4}$ alkyl.

In one embodiment of the present application, provided is a compound of Formula (I) or a pharmaceutically acceptable salt thereof, wherein:
X is selected from the group consisting of NR⁶ and O;
R¹ and R² are independently selected from the group consisting of hydrogen, halo, and $C_{1-4}$ alkyl;
R³ is $C_{1-4}$ alkoxy;
R⁴ is selected from the group consisting of [2-(dimethylamino)ethyl](methyl)amino, (2-hydroxyethyl)(methyl)amino and morpholin-4-yl;
R⁵ is selected from the group consisting of hydrogen, $C_{1-4}$ alkyl and $C_{1-3}$ alkoxy$C_{1-3}$ alkyl;
R⁶ is selected from the group consisting of hydrogen and $C_{1-4}$ alkyl.

In one embodiment of the present application, provided is a compound of Formula (I) or a pharmaceutically acceptable salt thereof, wherein:
X is selected from the group consisting of NR⁶ and O;
R¹ and R² are independently selected from the group consisting of hydrogen, chloro, bromo, fluoro and methyl;
R³ is methoxy;
R⁴ is selected from the group consisting of [2-(dimethylamino)ethyl](methyl)amino, (2-hydroxyethyl)(methyl)amino and morpholin-4-yl;
R⁵ is selected from the group consisting of hydrogen and methoxymethyl;
R⁶ is selected from the group consisting of hydrogen and methyl.

In some embodiments of the present application, the compounds of Formula (I) of the present application include the following compounds or pharmaceutically acceptable salts thereof:

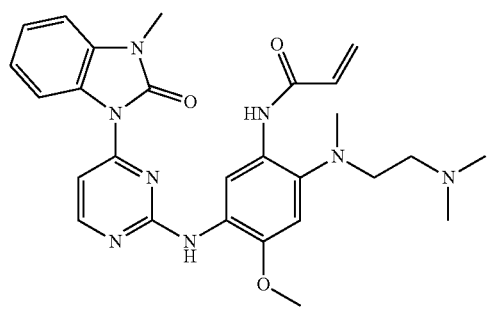

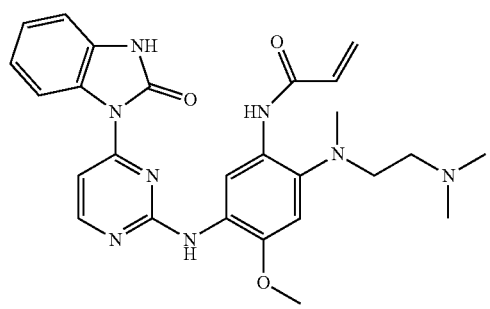

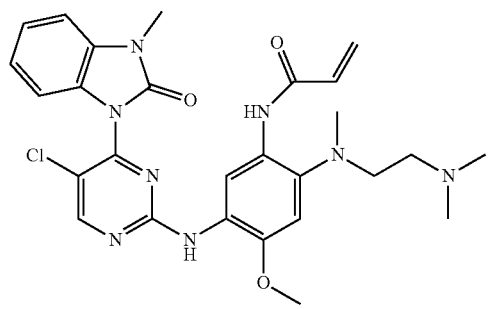

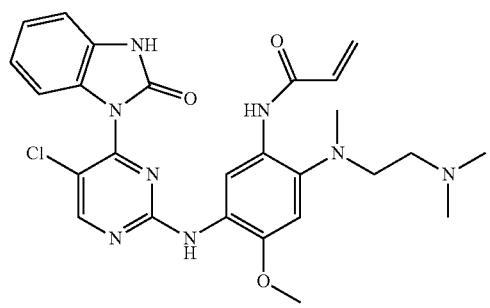

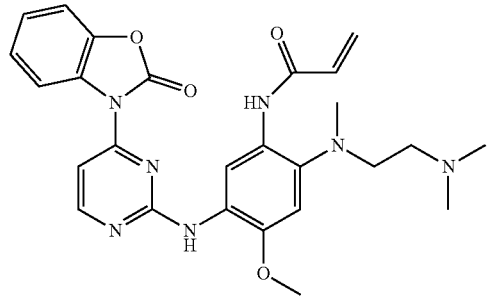

11
-continued
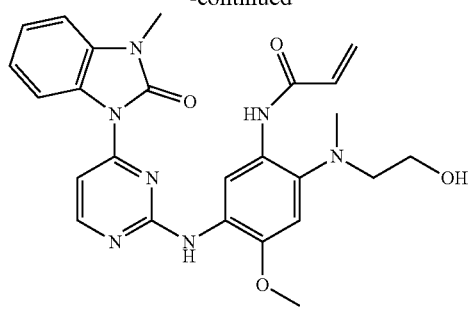
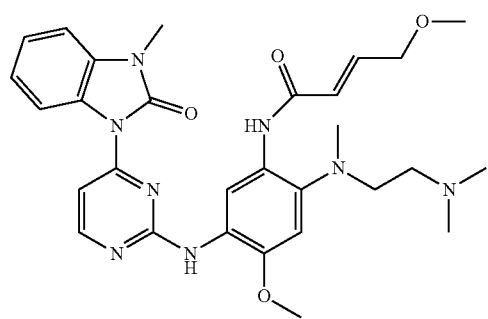
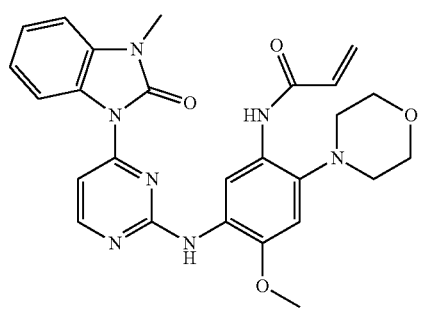
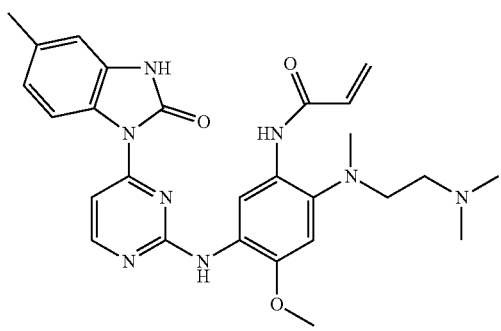
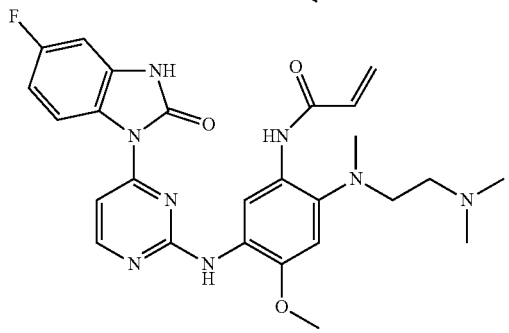
12
-continued
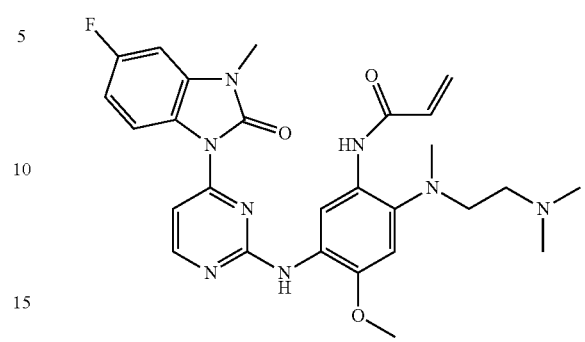
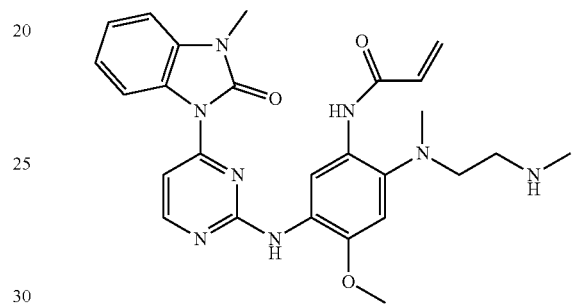
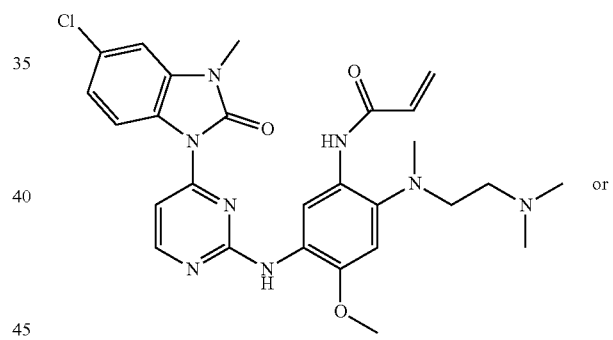
or
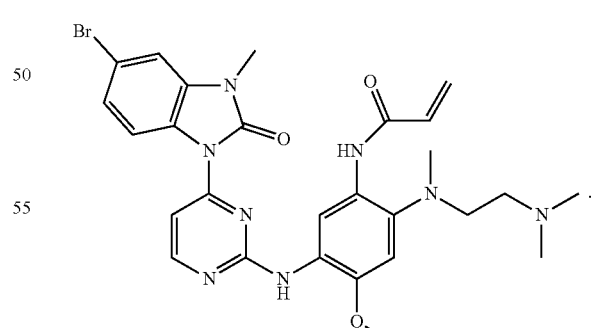
In some embodiments of the present application, the pharmaceutically acceptable salts of the compounds of Formula (I) of the present application include the following hydrochloride salts of the compounds:

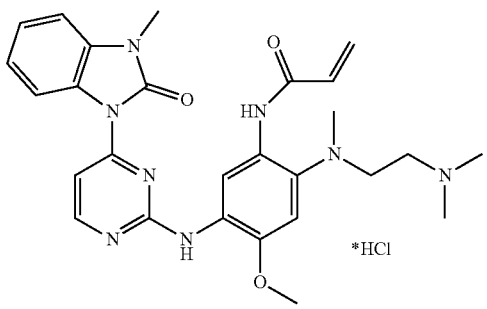
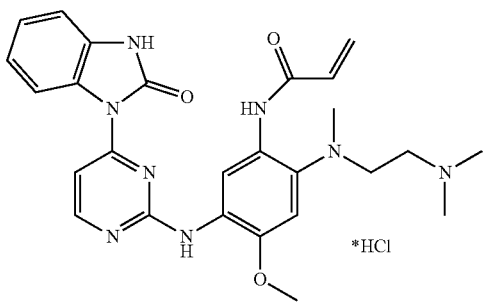
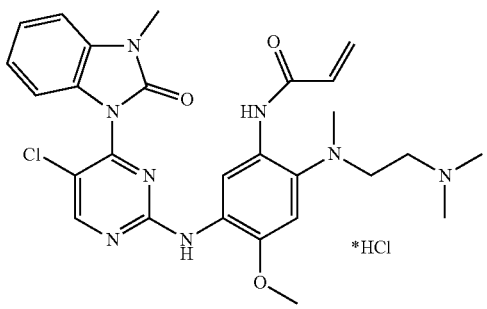
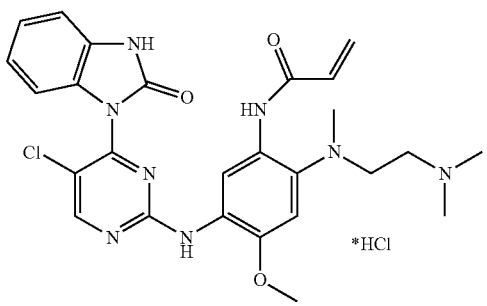
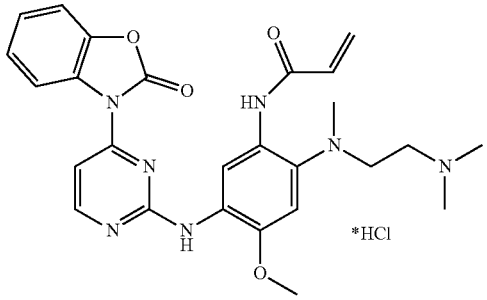
-continued
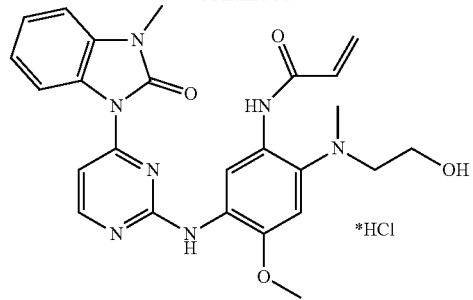
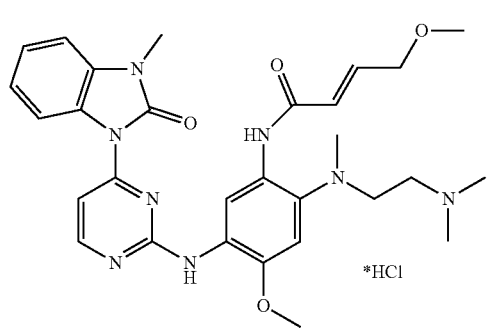
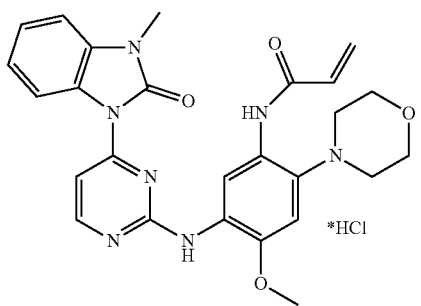
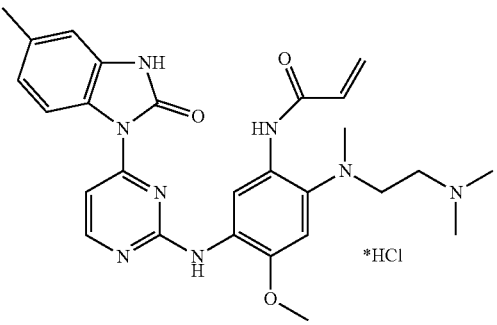
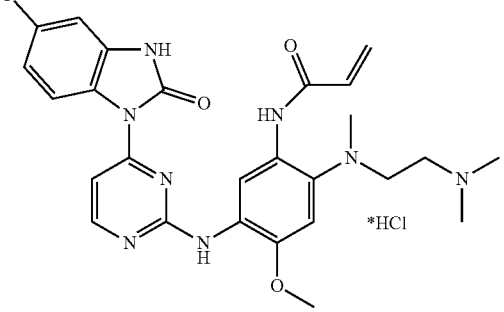

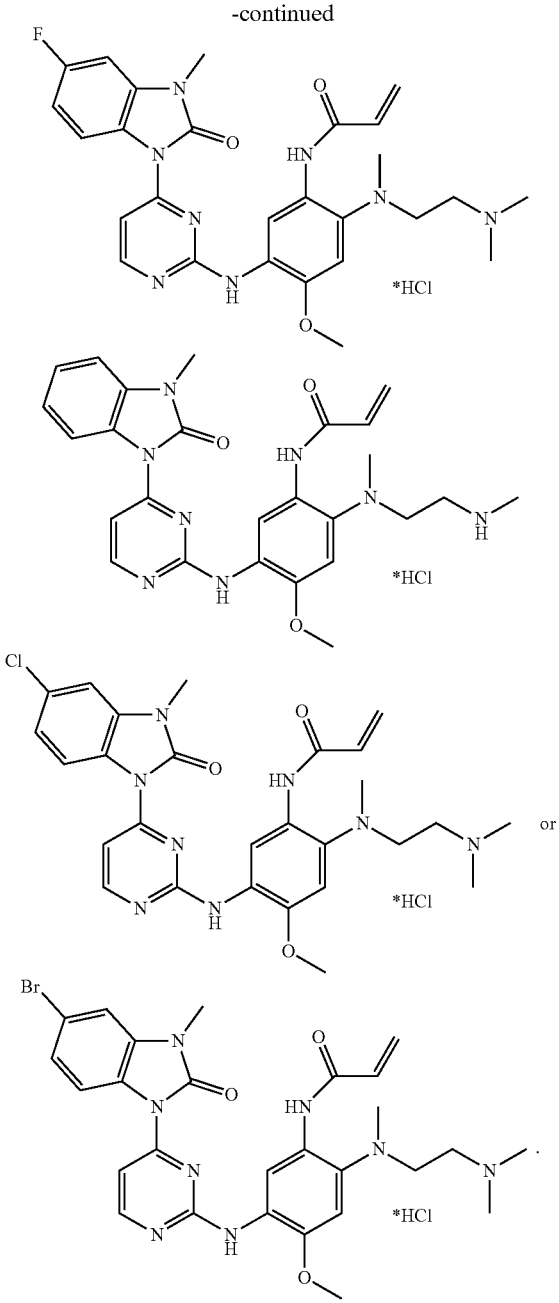

In another aspect, the present application provides a pharmaceutical composition comprising a compound represented by Formula (I) or a pharmaceutically acceptable salt thereof, and one or more pharmaceutically acceptable carriers or excipients. The pharmaceutical composition of the present application may further comprise one or more additional therapeutic agents.

In still another aspect, the present application provides a method for treating an EGFR-mediated disease, comprising administering to a subject in need thereof a compound of Formula (I) of the present application or a pharmaceutically acceptable salt thereof, or a pharmaceutical composition comprising the same.

In yet another aspect, the present application provides use of a compound of Formula (I) of the present application or a pharmaceutically acceptable salt thereof, or a pharmaceutical composition comprising the same, in the manufacture of a medicament for the treatment of an EGFR-mediated disease.

In some embodiments of the present application, the EGFR-mediated disease is selected from diseases mediated by an EGFR-L858R activating mutation.

In some embodiments of the present application, the EGFR-mediated disease is selected from diseases mediated by an EGFR-T790M activating mutation.

In some embodiments of the present application, the EGFR-mediated disease is selected from diseases mediated by EGFR-L858R+EGFR-T790M double-activating mutations.

In some embodiments of the present application, the EGFR-mediated disease is a cancer; the cancer is selected from the group consisting of ovarian cancer, cervical cancer, colorectal cancer, breast cancer, pancreatic cancer, glioma, glioblastoma, melanoma, prostate cancer, leukemia, lymphoma, non-Hodgkin's lymphoma, stomach cancer, lung cancer, hepatocellular cancer, stomach cancer, gastrointestinal stromal tumor, thyroid cancer, cholangiocarcinoma, endometrial cancer, kidney cancer, anaplastic large cell lymphoma, acute myeloid leukemia, multiple myeloma, melanoma, and mesothelioma; the lung cancer may be selected from non-small cell lung cancer, small cell lung cancer, lung adenocarcinoma and squamous cell lung cancer.

The pharmaceutical composition of the present application can be prepared by combining a compound of the present application or a salt thereof with a suitable pharmaceutically acceptable carrier, and may be formulated into, for example, solid, semi-solid, liquid or gaseous formulations, such as tablets, pills, capsules, powders, granules, pastes, emulsions, suspensions, solutions, suppositories, injections, inhalants, gels, microspheres, aerosols and the like.

Typical administration routes of the compound of the present application or a pharmaceutically acceptable salt thereof, or a pharmaceutical composition comprising the same, include, but are not limited to, oral, rectal, transmucosal, or enteral administration, or topical, transdermal, inhaled, parenteral, sublingual, intravaginal, intranasal, intraocular, intraperitoneal, intramuscular, subcutaneous, or intravenous administration.

The pharmaceutical composition of the present application can be manufactured through the well-known methods in the art, such as a conventional mixing method, dissolving method, granulation method, sugar-coated-pill method, grinding method, emulsification method, and freeze-drying method, etc.

For oral administration, the active compound can be mixed with the pharmaceutically acceptable carriers known in the art, to prepare the pharmaceutical composition. With these carriers, the compounds of the present application can be formulated into tablets, pills, lozenges, sugar-coated tablets, capsules, liquid, gels, syrup, or suspensions and the like, for oral administration to patients.

The solid oral composition can be prepared by conventional mixing, filling or compressing method. For example, it can be obtained through the following method: the active compound is mixed with solid excipients; optionally the resulting mixture is ground, and other suitable excipients are added if needed; then the mixture is processed into granules, so that the core of tablets or sugar-coated tablets is obtained. Suitable excipients include, but are not limited to, adhesives, diluents, disintegrants, lubricants, glidants, sweeteners and/or flavoring agents, etc., such as microcrystalline cellulose, glucose solutions, acacia mucilage, gelatin solutions, sucrose and/or starch pastes; talc, starch, magnesium stearate, calcium stearate and/or stearic acid; lactose, sucrose, starch, mannitol, sorbitol and/or dicalcium phosphate; silica; crosslinked sodium carboxymethylcellulose, pre-gelatinized starch, sodium starch glycolate, alginic acid, corn starch, potato starch, methyl cellulose, agar, carboxymethyl cellulose, and/or crosslinked polyvinylpyrrolidone, etc. Optionally, the core of the sugar-coated tablet can be coated through the well-known methods in general pharmaceutical practice, and enteric coating is particularly used.

The pharmaceutical composition is also suitable for parenteral administration, such as sterile solutions, suspensions or freeze-dried products in an adequate unit dose form.

In some embodiments, the compound of Formula (I) as described herein or a pharmaceutically acceptable salt thereof can be administered by any suitable routes and methods, for example, by oral or parenteral (e.g., intravenous) administration. Therapeutically effective amounts of the compound of Formula (I) are from about 0.0001 to 20 mg/Kg body weight per day, such as from 0.001 to 10 mg/Kg body weight per day.

In some embodiments, the frequency of dosage of the compound of Formula (I) is determined by the needs of the individual patient and can be, for example, once or twice per day, or more times per day. Administration can be intermittent, for example, with a period of several days during which a patient receives a daily dose of a compound of Formula (I), followed by a period of several days during which a patient does not receive a daily dose of the compound of Formula (I).

The compounds of the present application can be prepared by a variety of synthetic processes well known to those skilled in the art, including the specific embodiments listed below, embodiments formed by combining the specific embodiments with other chemical synthetic processes, and equivalent alternatives known to a person skilled in the art. Specific embodiments include, but are not limited to, the examples of the present application.

The chemical reaction of a specific embodiment of the present application is carried out in a suitable solvent, and the solvent should be suitable for the chemical changes of the present application and the required reagents and materials thereof. In order to obtain the compounds of the present application, a person skilled in the art sometimes needs to modify or select a synthesis step or a reaction process on the basis of the present embodiments.

In a specific embodiment, a part of the compounds of Formula (I) of the present application may be prepared by a person skilled in the field of organic synthesis with standard methods according to the following Scheme 1:

Scheme 1

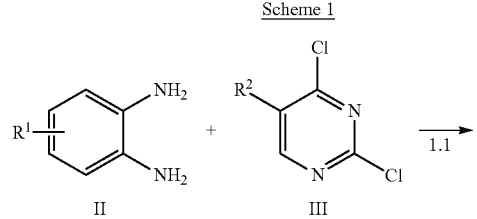

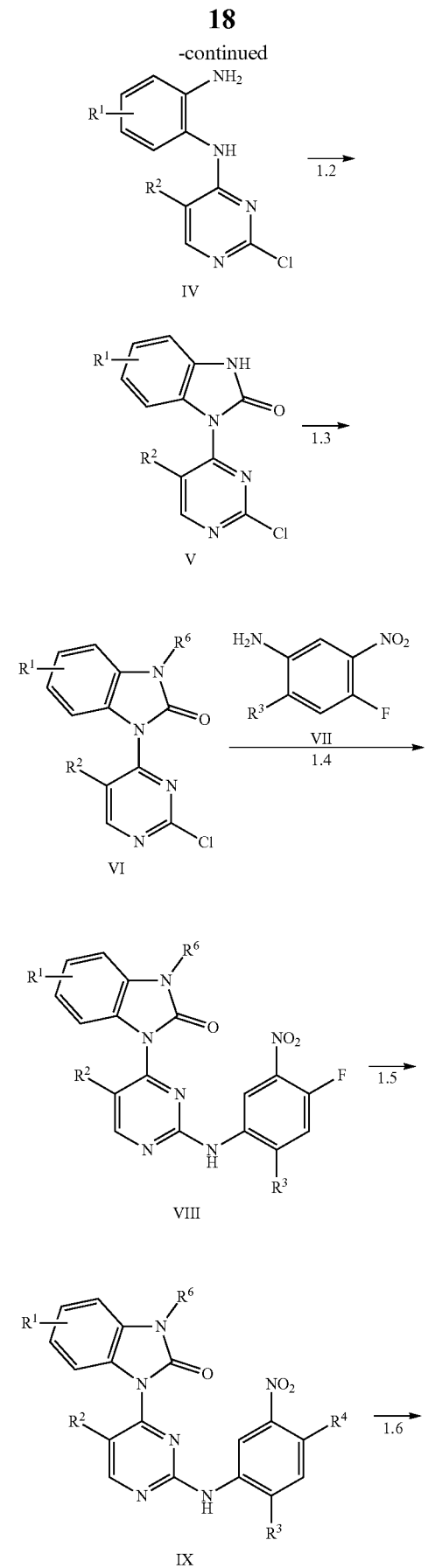

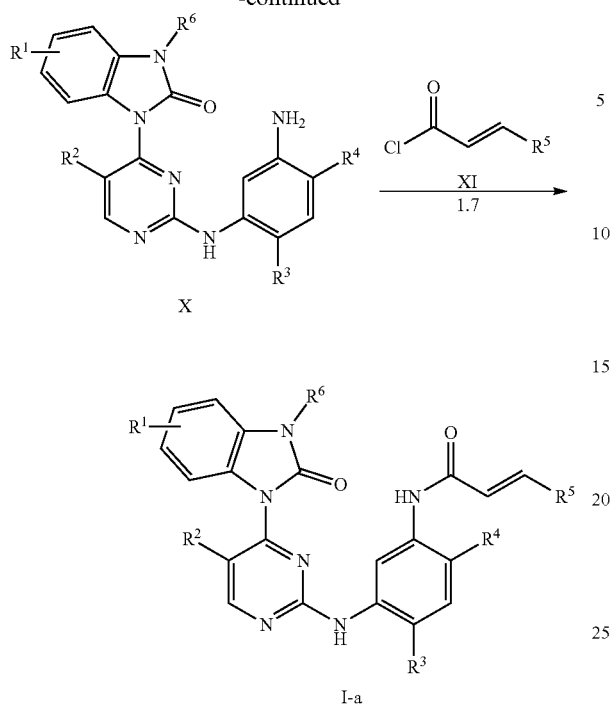

Starting from a compound of Formula (II) and a compound of Formula (III), a substitution reaction between the amino group on the benzene ring of the compound of Formula (II) and the chlorine atom on the pyrimidine of the compound of Formula (III) occurs first, and then a compound of Formula (IV) constructs a carbonyl group and forms a ring structure to obtain a compound of Formula (V), which then is attached to $R^6$ to obtain a compound of Formula (VI). The chlorine atom on the pyrimidine ring of the compound of Formula (VI) is reacted with the amino group on the benzene ring of a compound of Formula (VII) to obtain a compound of Formula (VIII), which then is attached to a side chain $R^4$ to obtain a compound of Formula (IX). The nitro group of the compound of Formula (IX) is reduced to an amino group, which then forms an amide bond with a compound of Formula (XI) to give a compound of Formula (I-a) as a final product.

A part of the compounds of Formula (I) of the present application may also be prepared by a person skilled in the field of organic synthesis with standard methods according to the following Scheme 2:

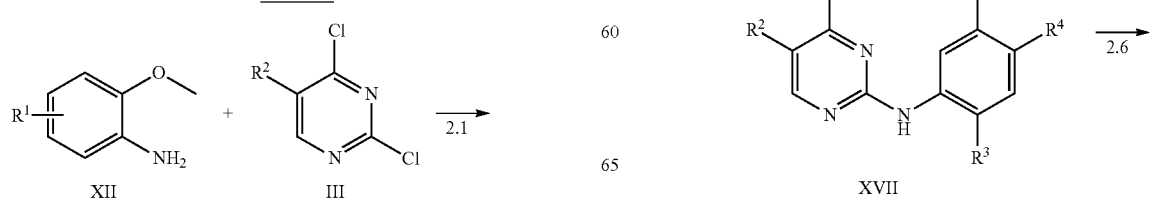

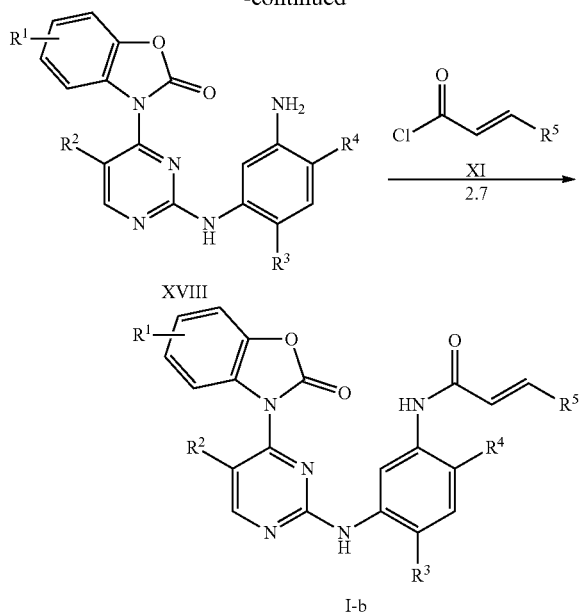

Starting from a compound of Formula (XII) and a compound of Formula (III), a substitution reaction between the amino group on the benzene ring of the compound of Formula (XII) and the chlorine atom on the pyrimidine of the compound of Formula (III) occurs first, and then methyl is removed from a compound of Formula (XIII) to obtain a compound of Formula (XIV), which then constructs a carbonyl group and forms a ring structure to obtain a compound of Formula (XV). A substitution reaction between the chlorine atom on the pyrimidine ring of the compound of Formula (XV) and the amino group on the benzene ring of the compound of Formula (VII) occurs to obtain a compound of Formula (XVI), which then is attached to a side chain $R^4$ to obtain a compound of Formula (XVII). The nitro group of the compound of Formula (XVII) is reduced to an amino group, which then forms an amide bond with a compound of Formula (XI) to give a compound of Formula (I-b) as a final product.

In some embodiments of the present application, those skilled in the art may prepare the compounds of the present application according to the steps of Scheme 1 or Scheme 2 without strictly following them. In view of the structure of the final product, the order of the steps in Scheme 1 or Scheme 2 can be varied, and steps can be added or omitted, which are also within the scope of the present application.

For clarity, examples are used to further illustrate the present application, but should not be considered as a definition or limitation to the scope of the present application.

The solvents used in the present application are commercially available and can be used without further purification. All operations involving moisture and/or oxygen sensitive experiments were conducted under nitrogen atmosphere in pre-dried glassware. Unless noted otherwise, all the materials were obtained from commercially available sources and used without further purification. Column chromatography used in the present application was performed on silica gel (200-300 mesh) produced by Qingdao Haiyang Chemical CO., LTD. Thin layer chromatography was performed using precoated chromatography plates purchased from E. Merck (silica gel 60PF254, 0.25 mm). The instrument used for nuclear magnetic resonance spectroscopy analysis was Varian VNMRS-400 resonance spectrometer. Chemical shift was referenced against the internal standard, tetramethylsilane (TMS=δ 0.00). The data of H-NMR spectrum were recorded as the following format: number of protons, peak pattern (s, singlet; d, doublet; t, triplet; q, quarter; m, multiplet), coupling constant (in terms of Hz).

The following abbreviations are used in the present application: DMF means N,N-dimethylformamide; NMP means N-methylpyrrolidone; DCM means dichloromethane; PE means petroleum ether; EA means ethyl acetate; MeOH means methanol; $Pd_2(dba)_3$ means tris(dibenzylideneacetone)dipalladium; TsOH means p-toluenesulfonic acid; BINAP means (±)-2,2'-bis-(diphenylphosphino)-1,1'-binaphthyl.

The compounds are nominated manually or by the ChemDraw® software. For the commercially available compounds, their names provided in the catalogs of the suppliers are used.

EXAMPLES

The purpose of the following specific examples is to facilitate those skilled in the art to more clearly understand and implement the present application. They should not be construed as limiting the scope of the present application, and they are merely exemplary illustrations and typical representatives of the present application.

Example 1: N-(2-((2-(dimethylamino)ethyl)(methyl)amino)-4-methoxy-5-(4-(3-methyl-2-oxo-2,3-dihydro-1H-benzo[d]imidazol-1-yl)pyrimidin-2-ylamino)phenyl)acrylamide Hydrochloride

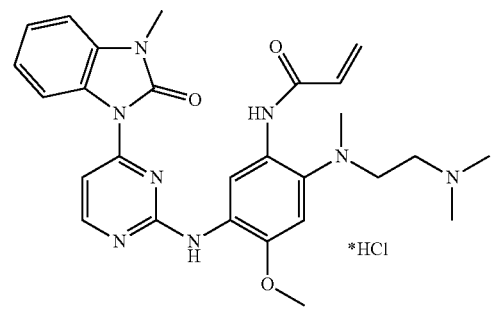 [SMILES: C=CC(=O)Nc1cc(Nc2nccc(-n3c(=O)n(C)c4ccccc43)n2)c(OC)cc1N(C)CCN(C)C]

Step 1: $N^1$-(2-chloropyrimidin-4-yl)benzene-1,2-diamine

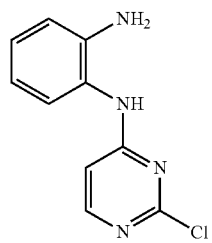 [SMILES: Nc1ccccc1Nc1ccnc(Cl)n1]

O-phenylenediamine (3.24 g, 30 mmol) and 2,4-dichloropyrimidine (4.47 g, 30 mmol) were dispersed in anhydrous ethanol (60 mL), and diisopropylethylamine (7.74 g, 60 mmol) was added thereto and the resulting mixture was heated to reflux for 3 hours. The resulting mixture was concentrated under vacuum to remove the solvent, and the residue was dissolved in dichloromethane (100 mL), washed with water and then saturated brine, and concentrated under vacuum to remove the solvent. The resulting residue was separated by column chromatography (EA:PE=1:2) to give the title compound (5.32 g, 80%).

$^1$H NMR (CDCl$_3$): δ 8.08 (1H, d, J=5.6 Hz), 7.20-7.12 (2H, m), 6.85-6.78 (2H, m), 6.74 (1H, s), 6.24 (1H, d, J=5.6 Hz), 3.82 (2H, br).

Step 2: 1-(2-chloropyrimidin-4-yl)-1H-benzo[d]imidazol-2(3H)-one

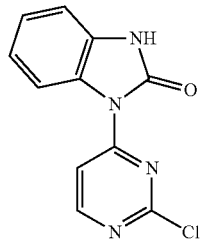 [SMILES: O=c1[nH]c2ccccc2n1-c1ccnc(Cl)n1]

N$^1$-(2-chloropyrimidin-4-yl)phenyl-1,2-diamine (2.21 g, 10 mmol) was dissolved in DMF (15 mL), and carbonyldiimidazole (2.43 g, 15 mmol) was added thereto and the resulting mixture was stirred at room temperature for 1 hour. The resulting mixture was poured into water (50 mL) and stirring was continued for 10 minutes. Then the resulting mixture was suction-filtered, and the filter cake was washed with water (30 mL*3), and dried to give the title compound (2.23 g, 90%).

$^1$H NMR (DMSO-d$_6$): δ 11.64 (1H, br), 8.78 (1H, d, J=5.6 Hz), 8.43 (1H, d, J=5.6 Hz), 8.26 (1H, d, J=7.6 Hz), 7.22-7.10 (3H, m).

Step 3: 1-(2-chloropyrimidin-4-yl)-3-methyl-1H-benzo[d]imidazol-2(3H)-one

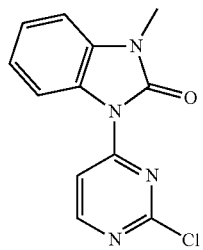 [SMILES: Cn1c(=O)n(-c2ccnc(Cl)n2)c2ccccc21]

1-(2-Chloropyrimidin-4-yl)-1H-benzo[d]imidazol-2(3H)-one (600 mg, 2.43 mmol) was dispersed in anhydrous DMF (10 mL) and cooled in an ice-water bath. Sodium hydride (116 mg, 60%, 2.90 mmol) was added thereto and the resulting mixture was stirred for 1 hour. Then iodomethane (345 mg, 2.43 mmol) was added dropwise and stirring was continued for 1 hour. The reaction solution was poured into water (50 mL), the resulting mixture was stirred for 30 minutes and then suction-filtered, and the filter cake was washed with water (30 mL*3) and dried to give the title compound (459 mg, 72%).

$^1$H NMR (DMSO-d$_6$): δ 8.79 (1H, d, J=5.6 Hz), 8.44 (1H, d, J=6.0 Hz), 8.29 (1H, d, J=8.0 Hz), 7.30-7.28 (2H, m), 7.24-7.19 (1H, m), 3.39 (3H, s).

Step 4: 1-(2-(4-fluoro-2-methoxy-5-nitrophenylamino)pyrimidin-4-yl)-3-methyl-1H-benzo[d]imidazol-2(3H)-one p-toluenesulfonate

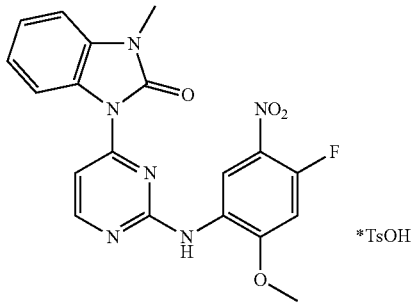 [SMILES: COc1cc(F)c([N+](=O)[O-])cc1Nc1nccc(-n2c(=O)n(C)c3ccccc32)n1]

1-(2-Chloropyrimidin-4-yl)-3-methyl-1H-benzo[d]imidazol-2(3H)-one (459 mg, 1.76 mmol), 4-fluoro-2-methoxy-5-nitroaniline (360 mg, 1.93 mmol) and p-toluenesulfonic acid monohydrate (551 mg, 2.89 mmol) were dispersed in 2-pentanol (10 mL) and the reaction mixture was stirred overnight at 105° C. After being cooled, the mixture was suction-filtered, and the filter cake was washed three times with a small amount of 2-pentanol and dried to give the title compound (440 mg, 43%).

$^1$H NMR (CDCl$_3$): δ 10.95 (1H, br), 8.49 (1H, d, J=7.6 Hz), 8.39 (1H, d, J=7.2 Hz), 8.21 (1H, d, J=7.2 Hz), 7.87 (2H, d, J=8.4 Hz), 7.68 (1H, d, J=8.4 Hz), 7.28-7.23 (2H, m), 7.04 (2H, d, J=7.6 Hz), 6.91-6.85 (2H, m), 3.92 (3H, s), 3.46 (3H, s), 2.38 (3H, s).

Step 5: 1-(2-(4-((2-(dimethylamino)ethyl)(methyl)amino)-2-methoxy-5-nitrophenylamino)pyrimidin-4-yl)-3-methyl-1H-benzo[d]imidazol-2(3H)-one

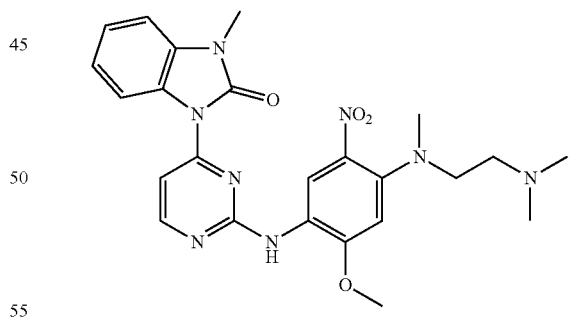

1-(2-(4-Fluoro-2-methoxy-5-nitrophenylamino)pyrimidin-4-yl)-3-methyl-1H-benzo[d]imidazol-2(3H)-one p-toluenesulfonate (440 mg, 0.76 mmol) was dissolved in NMP (5 mL). Diisopropylethylamine (206 mg, 1.59 mmol) and N$^1$,N$^1$,N$^2$-trimethylethane-1,2-diamine (116 mg, 1.14 mmol) were added thereto, and the reaction mixture was stirred overnight at 85° C. The reaction solution was cooled and then poured into water (50 mL). Then the mixture was suction-filtered, and the filter cake was rinsed with a small amount of methanol, and dried to give the title compound (326 mg, 88%).

¹H NMR (CDCl₃): δ 8.92 (1H, s), 8.51 (1H, d, J=5.6 Hz), 8.27 (1H, d, J=7.6 Hz), 7.82 (1H, d, J=5.6 Hz), 7.47 (1H, s), 7.29-7.19 (1H, m), 7.17-7.13 (1H, m), 7.04 (1H, d, J=7.6 Hz), 6.69 (1H, s), 3.98 (3H, s), 3.47 (3H, s), 3.27 (2H, t, J=7.2 Hz), 2.89 (3H, s), 2.88 (2H, t, J=7.2 Hz), 2.26 (6H, s).

Step 6: 1-(2-(5-amino-4-((2-(dimethylamino)ethyl) (methyl)amino)-2-methoxyphenylamino)pyrimidin-4-yl)-3-methyl-1H-benzo[d]imidazol-2(3H)-one

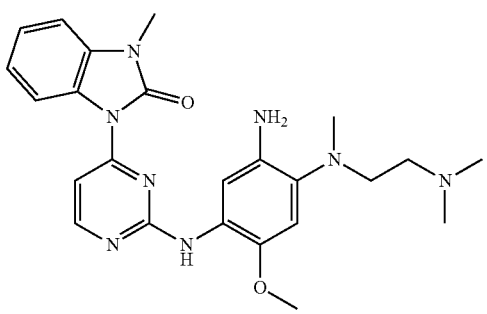 [SMILES: COc1cc(N(C)CCN(C)C)c(N)cc1Nc1nccc(-n2c(=O)n(C)c3ccccc32)n1]

1-(2-(4-((2-(Dimethylamino)ethyl)(methyl)amino)-2-methoxy-5-nitrophenylamino) pyrimidin-4-yl)-3-methyl-1H-benzo[d]imidazol-2(3H)-one (326 mg, 0.66 mmol) was dissolved in methanol (10 mL), and Pd/C (10%, 30 mg) was added thereto. After the air atmosphere was replaced with hydrogen for three times, the system was stirred overnight under hydrogen atmosphere and then suction-filtered. The product is easy to be oxidized, and therefore the resulting filtrate was rapidly concentrated under vacuum and then directly fed to the next reaction step.

Step 7: N-(2-((2-(dimethylamino)ethyl)(methyl) amino)-4-methoxy-5-(4-(3-methyl-2-oxo-2,3-dihydro-1H-benzo[d]imidazol-1-yl)pyrimidin-2-ylamino)phenyl)acrylamide Hydrochloride

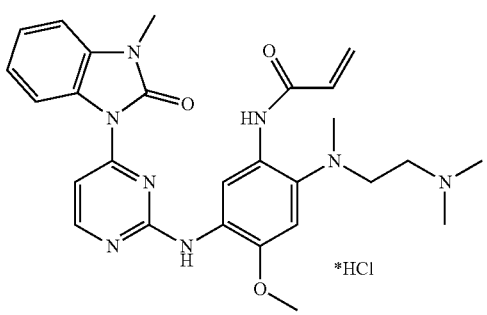 [SMILES: C=CC(=O)Nc1cc(Nc2nccc(-n3c(=O)n(C)c4ccccc43)n2)c(OC)cc1N(C)CCN(C)C]

1-(2-(5-Amino-4-((2-(dimethylamino)ethyl)(methyl) amino)-2-methoxyphenylamino) pyrimidin-4-yl)-3-methyl-1H-benzo[d]imidazol-2(3H)-one obtained from the previous step was dissolved in anhydrous dichloromethane (10 mL), and diisopropylethylamine (129 mg, 1.00 mmol) was added thereto and cooled in an ice-water bath. A solution of acryloyl chloride (60 mg, 0.66 mmol) in anhydrous dichloromethane (2 mL) was slowly added dropwise to the system over 15 minutes. After stirred for additional 15 minutes, the reaction solution was poured into petroleum ether (50 mL) and stirred for 10 minutes. The resulting mixture was suction-filtered, and the filter cake was rinsed with petroleum ether. The resulting crude product was separated by column chromatography (DCM:MeOH=20:1) to give the title compound (164 mg, 45% yield over two steps).

¹H NMR (DMSO-d₆): δ 10.15 (1H, br), 9.72 (1H, br), 8.70 (1H, s), 8.41 (1H, d, J=5.6 Hz), 8.16-8.12 (2H, m), 7.67 (1H, d, J=5.6 Hz), 7.22-7.12 (2H, m), 6.99-6.92 (3H, m), 6.19 (1H, dd, J=2.0 Hz, 17.2 Hz), 5.68 (1H, dd, J=2.0 Hz, 10.4 Hz), 3.77 (3H, s), 3.34 (3H, s), 3.28 (4H, br), 2.72 (6H, s), 2.60 (3H, s).

Example 2: N-(2-((2-(dimethylamino)ethyl)(methyl) amino)-4-methoxy-5-(4-(2-oxo-2,3-dihydrobenzo[d] imidazol-1-yl)pyrimidin-2-ylamino)phenyl)acrylamide Hydrochloride

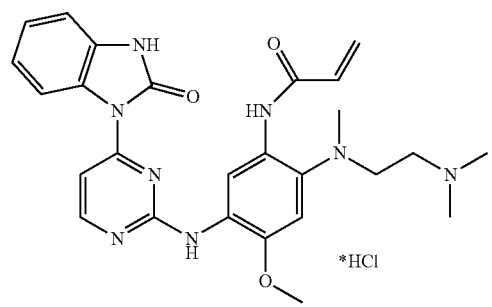 [SMILES: C=CC(=O)Nc1cc(Nc2nccc(-n3c(=O)[nH]c4ccccc43)n2)c(OC)cc1N(C)CCN(C)C]

Step 1: 1-(2-(4-fluoro-2-methoxy-5-nitrophenylamino)pyrimidin-4-yl)-1H-benzo[d]imidazol-2 (3H)-one p-toluenesulfonate

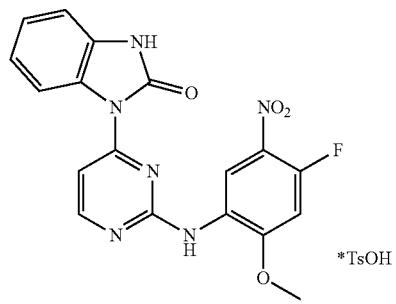 [SMILES: COc1cc(F)c([N+](=O)[O-])cc1Nc1nccc(-n2c(=O)[nH]c3ccccc32)n1]

The title compound was prepared from 1-(2-chloropyrimidin-4-yl)-1H-benzo[d] imidazol-2(3H)-one and 4-fluoro-2-methoxy-5-nitroaniline by a method similar to that described in Step 4 of Example 1.

¹H NMR (DMSO-d₆): δ 11.47 (1H, s), 9.12 (1H, s), 8.62 (1H, d, J=8.4 Hz), 8.50 (1H, d, J=5.6 Hz), 8.16-8.14 (1H, m), 7.82 (1H, d, J=5.6 Hz), 7.47-7.40 (3H, m), 7.15-7.09 (3H, m), 7.04 (1H, d, J=7.6 Hz), 6.95-6.91 (1H, m), 3.96 (3H, s), 2.27 (3H, s).

Step 2: 1-(2-(4-((2-(dimethylamino)ethyl)(methyl)amino)-2-methoxy-5-nitrophenylamino)pyrimidin-4-yl)-1H-benzo[d]imidazol-2(3H)-one

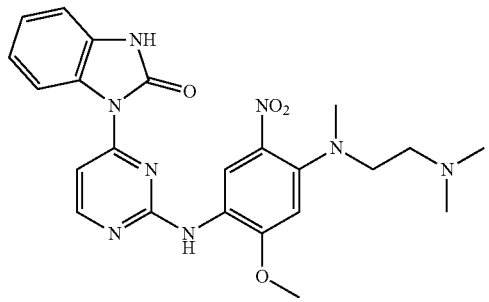 [SMILES: COc1cc(N(C)CCN(C)C)c([N+](=O)[O-])cc1Nc1nccc(-n2c(=O)[nH]c3ccccc32)n1]

The title compound was prepared from 1-(2-(4-fluoro-2-methoxy-5-nitrophenylamino)pyrimidin-4-yl)-1H-benzo[d]imidazol-2(3H)-one p-toluenesulfonate by a method similar to that described in Step 5 of Example 1.

$^1$H NMR (DMSO-$d_6$): δ 11.39 (1H, s), 8.72 (1H, s), 8.42 (1H, d, J=5.6 Hz), 8.12-8.03 (2H, m), 7.68 (1H, d, J=5.6 Hz), 7.11-7.07 (1H, m), 7.02-7.00 (1H, m), 6.88-6.84 (1H, m), 6.81 (1H, s), 3.87 (3H, s), 3.28 (2H, t, J=6.8 Hz), 2.85 (3H, s), 2.46 (2H, t, J=6.8 Hz), 2.15 (6H, s).

Step 3: N-(2-((2-(dimethylamino)ethyl)(methyl)amino)-4-methoxy-5-(4-(2-oxo-2,3-dihydro-1H-benzo[d]imidazol-1-yl)pyrimidin-2-ylamino)phenyl) acrylamide Hydrochloride

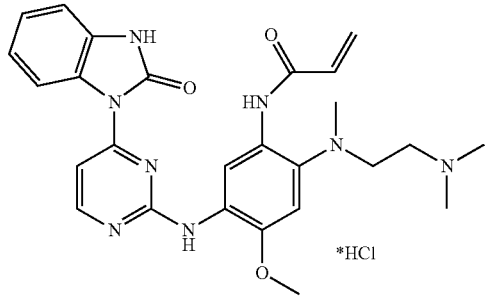 [SMILES: C=CC(=O)Nc1cc(Nc2nccc(-n3c(=O)[nH]c4ccccc43)n2)c(OC)cc1N(C)CCN(C)C]

The title compound was prepared from 1-(2-(4-((2-(dimethylamino)ethyl)(methyl) amino)-2-methoxy-5-nitrophenylamino)pyrimidin-4-yl)-1H-benzo[d]imidazol-2(3H)-one by a method similar to those described in Steps 6 and 7 of Example 1.

$^1$H NMR (MeOD): δ 8.46 (1H, d, J=5.6 Hz), 8.28 (1H, s), 8.14 (1H, d, J=8.4 Hz), 7.70 (1H, d, J=5.6 Hz), 7.12-7.06 (2H, m), 7.03-7.99 (1H, m), 6.97 (1H, s), 6.51-6.38 (2H, m), 5.83-5.80 (1H, m), 3.97 (3H, s), 3.45 (2H, br), 3.21 (2H, br), 2.81 (6H, s), 2.71 (3H, s).

Example 3: N-(5-(5-chloro-4-(3-methyl-2-oxo-2,3-dihydro-1H-benzo[d]imidazol-1-yl)pyrimidin-2-ylamino)-2-((2-(dimethylamino)ethyl)(methyl)amino)-4-methoxyphenyl) acrylamide Hydrochloride

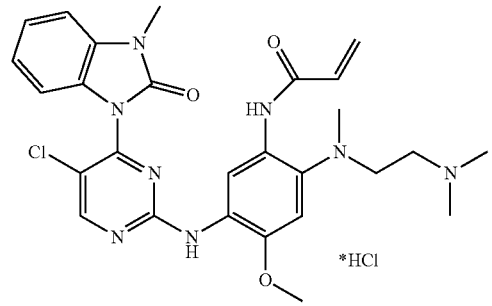 [SMILES: C=CC(=O)Nc1cc(Nc2ncc(Cl)c(-n3c(=O)n(C)c4ccccc43)n2)c(OC)cc1N(C)CCN(C)C]

Step 1: N$^1$-(2,5-dichloropyrimidin-4-yl)benzene-1,2-diamine

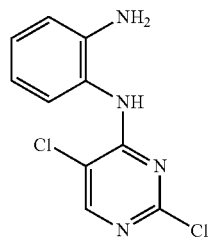 [SMILES: Nc1ccccc1Nc1nc(Cl)ncc1Cl]

The title compound was prepared from 2,4,5-trichloropyrimidine and o-phenylenediamine by a method similar to that described in Step 1 of Example 1.

$^1$H NMR (CDCl$_3$): δ 8.18 (1H, s), 7.46 (1H, dd, J=1.6 Hz, 7.2 Hz), 7.15-7.11 (2H, m), 6.91-6.86 (2H, m), 3.67 (2H, br).

Step 2: 1-(2,5-dichloropyrimidin-4-yl)-1H-benzo[d]imidazol-2(3H)-one

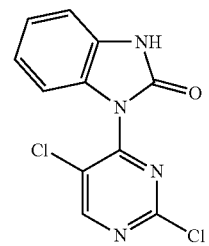 [SMILES: O=c1[nH]c2ccccc2n1-c1nc(Cl)ncc1Cl]

N$^1$-(2,5-dichloropyrimidin-4-yl)benzene-1,2-diamine (100 mg, 0.39 mmol) was dissolved in ethyl acetate (5 mL), and diisopropylethylamine (151 mg, 1.17 mmol) was added thereto and cooled in an ice-water bath. Then triphosgene (71 mg, 0.24 mmol) was added in batches. The resulting mixture was allowed to naturally warm to room temperature, and stirring was continued for 1 hour. Saturated sodium bicarbonate solution (10 mL) was added, and stirring was continued for 10 minutes. The mixture was extracted with ethyl acetate (20 mL*2), and the organic phases were combined, washed with saturated brine and concentrated under vacuum to remove the solvent to give the title compound (105 mg, 95%).

$^1$H NMR (DMSO-d$_6$): δ 11.44 (1H, br), 9.16 (1H, s), 7.20-7.04 (4H, m).

Step 3: 1-(2,5-dichloropyrimidin-4-yl)-3-methyl-1H-benzo[d]imidazol-2(3H)-one

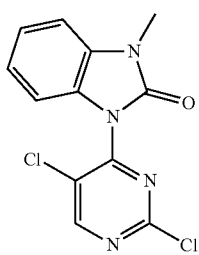

The title compound was prepared from 1-(2,5-dichloropyrimidin-4-yl)-1H-benzo[d]imidazol-2(3H)-one by a method similar to that described in Step 3 of Example 1.

$^1$H NMR (CDCl$_3$): δ 8.80 (1H, s), 7.27-7.23 (2H, m), 7.18-7.16 (1H, m), 7.06 (1H, d, J=8.0 Hz), 3.48 (3H, s).

Step 4: 1-(5-chloro-2-(4-fluoro-2-methoxy-5-nitrophenylamino)pyrimidin-4-yl)-3-methyl-1H-benzo[d]imidazol-2(3H)-one

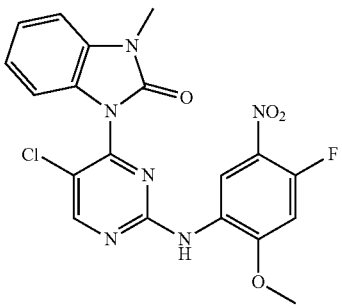 [SMILES: COc1cc(F)c([N+](=O)[O-])cc1Nc1ncc(Cl)c(-n2c(=O)n(C)c3ccccc32)n1]

1-(2,5-Dichloropyrimidin-4-yl)-3-methyl-1H-benzo[d]imidazol-2(3H)-one (50 mg, 0.17 mmol), 4-fluoro-2-methoxy-5-nitroaniline (63 mg, 0.34 mmol), BINAP (11 mg, 0.017 mmol) and cesium carbonate (110 mg, 0.34 mmol) were dispersed in anhydrous toluene (5 mL). After nitrogen gas was bubbled for 20 minutes, Pd$_2$(dba)$_3$ (8 mg, 0.008 mmol) was added. The system reacted for 1 hour in a microwave reactor (100 W, 100° C.) and concentrated under vacuum to remove the solvent. The resulting residue was separated by column chromatography (DCM to DCM:EA=20:1) to give the title compound (54 mg, 72%).

$^1$H NMR (CDCl$_3$): 9.31 (1H, s), 8.02 (1H, s), 8.55 (1H, d, J=8.2 Hz), 7.33 (1H, d, J=13.6 Hz), 7.25 (1H, d, J=7.2 Hz), 7.21-7.16 (2H, m), 6.78 (1H, d, J=12.0 Hz), 3.97 (3H, s), 3.43 (3H, s).

Step 5: 1-(5-chloro-2-(4-((2-(dimethylamino)ethyl)(methyl)amino)-2-methoxy-5-nitrophenylamino)pyrimidin-4-yl)-3-methyl-1H-benzo[d]imidazol-2(3H)-one

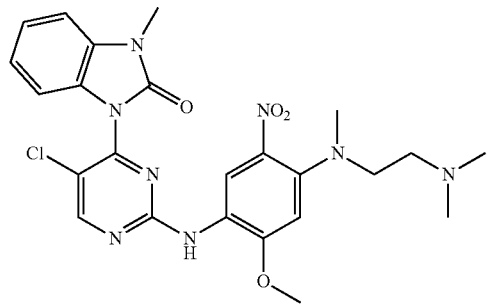 [SMILES: COc1cc(N(C)CCN(C)C)c([N+](=O)[O-])cc1Nc1ncc(Cl)c(-n2c(=O)n(C)c3ccccc32)n1]

The title compound was prepared from 1-(5-chloro-2-(4-fluoro-2-methoxy-5-nitrophenylamino)pyrimidin-4-yl)-3-methyl-1H-benzo[d]imidazol-2(3H)-one by a method similar to that described in Step 5 of Example 1.

$^1$H NMR (CDCl$_3$): δ 8.88 (1H, s), 8.59 (1H, s), 7.69 (1H, s), 7.25-7.19 (2H, m), 7.16-7.14 (1H, m), 7.05 (1H, d, J=7.2 Hz), 6.65 (1H, s), 3.95 (3H, s), 3.49 (3H, s) 3.25 (2H, t, J=7.2 Hz), 2.56 (3H, s), 2.54 (2H, t, J=7.2 Hz), 2.25 (6H, s).

Step 6: 1-(2-(5-amino-4-((2-(dimethylamino)ethyl)(methyl)amino)-2-methoxyphenylamino)-5-chloropyrimidin-4-yl)-3-methyl-1H-benzo[d]imidazol-2(3H)-one

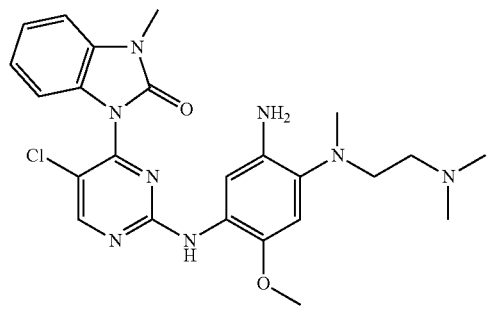

1-(5-Chloro-2-(4-((2-(dimethylamino)ethyl)(methyl)amino)-2-methoxy-5-nitrophenylamino)pyrimidin-4-yl)-3-methyl-1H-benzo[d]imidazol-2(3H)-one (320 mg, 0.61 mmol), iron powder (139 mg, 2.48 mmol) and ammonium chloride (50 mg, 0.93 mmol) were dispersed in a mixed solution of ethanol/water (8 mL/4 mL). The system was stirred vigorously at 80° C. for 3 hours, cooled and then filtered, and the organic solvent was removed under vacuum. To the resultant was added water (20 mL) and the resulting mixture was extracted with ethyl acetate (20 mL*3). The resulting organic phase was washed with saturated brine and concentrated under vacuum to remove the solvent to give the title compound, which was directly used in the next reaction step.

Step 7: N-(5-(5-chloro-4-(3-methyl-2-oxo-2,3-di-hydro-1H-benzo[d]imidazol-1-yl)pyrimidin-2-ylamino)-2-((2-(dimethylamino)ethyl)(methyl)amino)-4-methoxyphenyl) acrylamide Hydrochloride

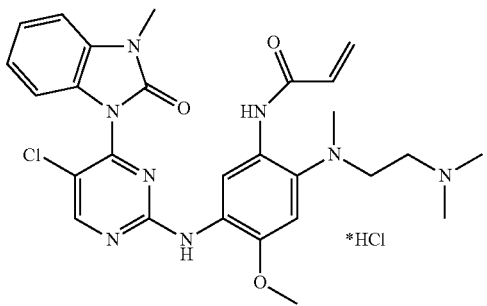 [SMILES: C=CC(=O)Nc1cc(Nc2ncc(Cl)c(-n3c(=O)n(C)c4ccccc43)n2)c(OC)cc1N(C)CCN(C)C]

The title compound was prepared from 1-(5-chloro-2-(4-((2-(dimethylamino)ethyl)(methyl)amino)-2-methoxy-5-nitrophenylamino)pyrimidin-4-yl)-3-methyl-1H-benzo[d]imidazol-2(3H)-one by a method similar to that described in Step 7 of Example 1.

$^1$H NMR (DMSO-$d_6$): δ 10.15 (1H, br), 9.68 (1H, br), 9.05 (1H, s), 8.66 (1H, s), 8.11 (1H, s), 7.23-7.20 (1H, m), 7.15-7.09 (2H, m), 7.05-6.99 (2H, m), 6.89 (1H, s), 6.41 (1H, dd, J=2.0 Hz, 16.8 Hz), 5.70 (1H, dd, J=2.0 Hz, 10.0 Hz), 3.79 (3H, s), 3.35 (3H, s), 3.28 (2H, br), 2.65 (6H, s), 2.55 (5H, s).

Example 4: N-(5-(5-chloro-4-(2-oxo-2,3-dihydro-1H-benzo[d]imidazol-1-yl)pyrimidin-2-ylamino)-2-((2-(dimethylamino)ethyl)(methyl)amino)-4-methoxyphenyl) acrylamide Hydrochloride

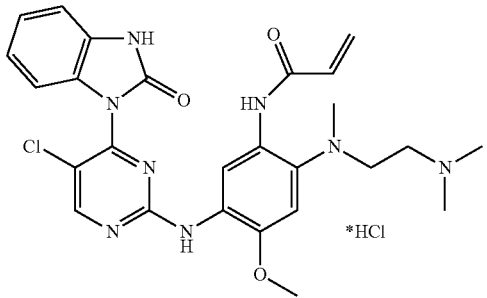 [SMILES: C=CC(=O)Nc1cc(Nc2ncc(Cl)c(-n3c(=O)[nH]c4ccccc43)n2)c(OC)cc1N(C)CCN(C)C]

Step 1: 1-(5-chloro-2-(4-fluoro-2-methoxy-5-nitrophenylamino)pyrimidin-4-yl)-1H-benzo[d]imidazol-2(3H)-one

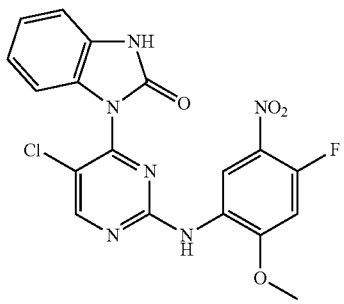 [SMILES: COc1cc(F)c([N+](=O)[O-])cc1Nc1ncc(Cl)c(-n2c(=O)[nH]c3ccccc32)n1]

The title compound was prepared from 1-(2,5-dichloropyrimidin-4-yl)-1H-benzo[d]imidazol-2(3H)-one and 4-fluoro-2-methoxy-5-nitroaniline by a method similar to that described in Step 4 of Example 3.

$^1$H NMR (CDCl$_3$): 9.24 (1H, d, J=8.0 Hz), 8.68 (1H, s), 8.45 (1H, s), 7.83 (1H, s), 7.34 (1H, s), 7.22-7.10 (3H, m), 6.78 (1H, d, J=12.0 Hz), 4.02 (3H, s).

Step 2: 1-(5-chloro-2-(4-((2-(dimethylamino)ethyl)(methyl)amino)-2-methoxy-5-nitrophenylamino)pyrimidin-4-yl)-1H-benzo[d]imidazol-2(3H)-one

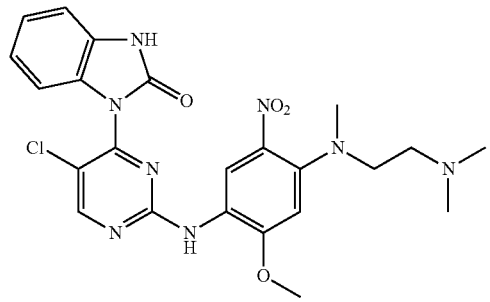 [SMILES: COc1cc(N(C)CCN(C)C)c([N+](=O)[O-])cc1Nc1ncc(Cl)c(-n2c(=O)[nH]c3ccccc32)n1]

$^1$H NMR (CDCl$_3$): δ 8.94 (1H, s), 8.66 (1H, s), 8.38 (1H, br), 7.84 (1H, s), 7.23-7.13 (4H, m), 4.05 (3H, s), 3.56 (2H, br), 3.08 (2H, br), 2.89 (3H, s) 2.69 (6H, s).

The title compound was prepared from 1-(5-chloro-2-(4-fluoro-2-methoxy-5-nitrophenylamino)pyrimidin-4-yl)-1H-benzo[d]imidazol-2(3H)-one by a method similar to that described in Step 5 of Example 1.

Step 3: N-(5-(5-chloro-4-(2-oxo-2,3-dihydro-1H-benzo[d]imidazol-1-yl)pyrimidin-2-ylamino)-2-((2-(dimethylamino)ethyl)(methyl)amino)-4-methoxyphenyl) acrylamide Hydrochloride

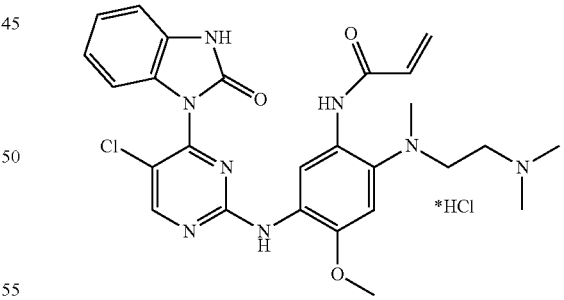

The title compound was prepared from 1-(5-chloro-2-(4-((2-(dimethylamino)ethyl)(methyl)amino)-2-methoxy-5-nitrophenylamino)pyrimidin-4-yl)-1H-benzo[d]imidazol-2(3H)-one by a method similar to those described in Steps 6 and 7 of Example 3.

$^1$H NMR (CDCl$_3$): δ 12.20 (1H, br), 9.35 (1H, br), 9.17 (1H, br), 8.64 (1H, s), 8.41 (1H, br), 7.69 (1H, s), 7.21-7.16 (1H, m), 7.13-7.07 (3H, m), 6.67 (1H, s), 6.42 (1H, dd, J=1.6 Hz, 16.8 Hz), 5.71 (1H, d, J=11.6 Hz), 3.84 (3H, s), 3.24 (2H, br), 3.08 (2H, br), 2.72 (9H, br).

Example 5: N-(2-((2-(dimethylamino)ethyl)(methyl)amino)-4-methoxy-5-(4-(2-oxobenzo[d]oxazol-3(2H)-yl)pyrimidin-2-ylamino)phenyl) acrylamide Hydrochloride

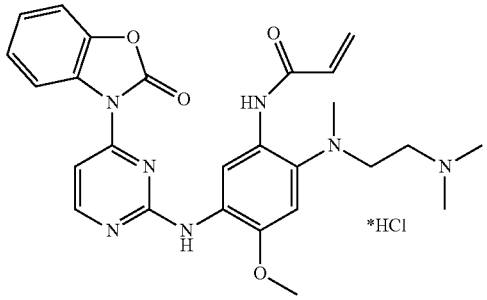 [SMILES: C=CC(=O)Nc1cc(Nc2nccc(-n3c(=O)oc4ccccc43)n2)c(OC)cc1N(C)CCN(C)C]

Step 1:
2-chloro-N-(2-methoxyphenyl)pyrimidin-4-amine

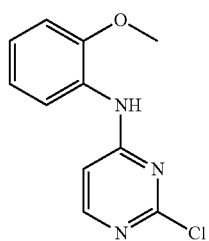 [SMILES: COc1ccccc1Nc1ccnc(Cl)n1]

The title compound was prepared from o-methoxyaniline and 2,4-dichloropyrimidine by a method similar to that described in Step 1 of Example 1.

$^1$H NMR (CDCl$_3$): δ 8.14 (1H, d, J=5.6 Hz), 7.83 (1H, br), 7.27 (1H, m), 7.17-7.13 (1H, m), 7.04-6.99 (1H, m), 6.96-6.94 (1H, m), 6.63-6.62 (1H, d, J=6.0 Hz), 3.89 (3H, s).

Step 2: 2-(2-chloropyrimidin-4-ylamino)phenol

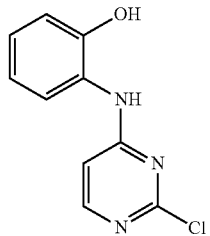 [SMILES: Oc1ccccc1Nc1ccnc(Cl)n1]

2-Chloro-N-(2-methoxyphenyl)pyrimidin-4-amine (100 mg, 0.42 mmol) was dissolved in anhydrous dichloromethane (3 mL) and cooled in an ice-water bath. A solution (2.5 mL, 2.12 mmol) of boron tribromide in dichloromethane was slowly added dropwise and the resulting mixture was allowed to naturally warm to room temperature, and stirring was continued for 2 hours. The reaction was quenched with the addition of saturated ammonium chloride solution, and then the mixture was extracted with dichloromethane (20 mL*3). The organic phases were combined and washed with saturated brine, and the solvent was removed under vacuum to give the title compound (84 mg, 89%).

$^1$H NMR (DMSO-d$_6$): δ 9.85 (1H, s), 9.31 (1H, s), 8.07 (1H, d, J=6.0 Hz), 7.57 (1H, br), 7.05-7.01 (1H, m), 6.93 (1H, d, J=8.0 Hz), 6.84-6.80 (1H, m), 6.66 (1H, br).

Step 3: 3-(2-chloropyrimidin-4-yl)benzo[d]oxazol-2(3H)-one

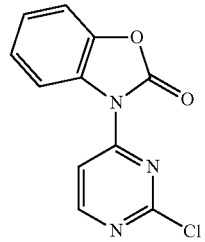 [SMILES: O=c1oc2ccccc2n1-c1ccnc(Cl)n1]

The title compound was prepared from 2-(2-chloropyrimidin-4-ylamino)phenol by a method similar to that described in Step 2 of Example 3.

$^1$H NMR (DMSO-d$_6$): δ 8.87 (1H, d, J=5.6 Hz), 8.25-8.19 (2H, m), 7.49 (1H, d, J=7.6 Hz), 7.39-7.30 (2H, m).

Step 4: 3-(2-(4-fluoro-2-methoxy-5-nitrophenylamino)pyrimidin-4-yl)benzo[d] oxazol-2(3H)-one p-toluenesulfonate

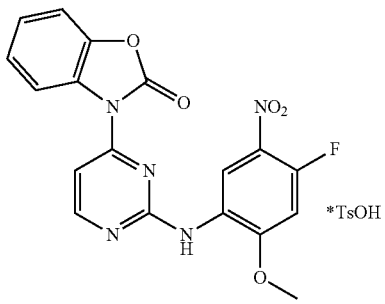 [SMILES: COc1cc(F)c([N+](=O)[O-])cc1Nc1nccc(-n2c(=O)oc3ccccc32)n1]

The title compound was prepared from 3-(2-chloropyrimidin-4-yl)benzo[d]oxazol-2(3H)-one by a method similar to that described in Step 4 of Example 1.

$^1$H NMR (DMSO-d$_6$): δ 10.83 (1H, br), 9.23 (1H, s), 8.59 (1H, d, J=5.6 Hz), 8.24 (1H, br), 7.64 (1H, d, J=5.6 Hz), 7.47-7.43 (4H, m), 7.31-7.24 (1H, m), 7.19-7.14 (1H, m), 7.11 (2H, d, J=8.0 Hz), 3.97 (3H, s), 2.28 (3H, s).

Step 5: 3-(2-(4-((2-(dimethylamino)ethyl)(methyl) amino)-2-methoxy-5-nitrophenylamino)pyrimidin-4-yl)benzo[d]oxazol-2(3H)-one

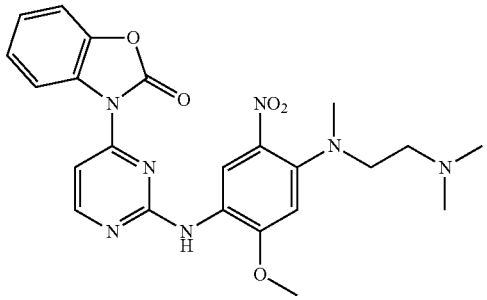 [SMILES: COc1cc(N(C)CCN(C)C)c([N+](=O)[O-])cc1Nc1nccc(-n2c(=O)oc3ccccc32)n1]

The title compound was prepared from 3-(2-(4-fluoro-2-methoxy-5-nitrophenylamino)pyrimidin-4-yl)benzo[d]oxazol-2(3H)-one p-toluenesulfonate by a method similar to that described in Step 5 of Example 1.

$^1$H NMR (CDCl$_3$): δ 8.86 (1H, s), 9.23 (1H, s), 8.57 (1H, d, J=5.6 Hz), 8.24-8.22 (1H, m), 7.74 (1H, d, J=5.6 Hz), 7.48 (1H, s), 7.29-7.25 (2H, m), 6.72 (1H, s), 4.01 (3H, s), 3.29 (2H, t, J=7.2 Hz), 2.89 (3H, s), 2.57 (2H, t, J=7.2 Hz), 2.27 (6H, s).

Step 6: N-(2-((2-(dimethylamino)ethyl)(methyl) amino)-4-methoxy-5-(4-(2-oxobenzo[d]oxazol-3(2H)-yl)pyrimidin-2-ylamino)phenyl)acrylamide Hydrochloride

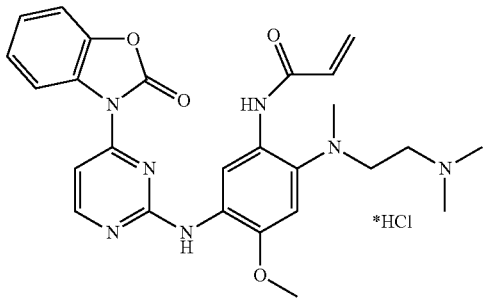 [SMILES: C=CC(=O)Nc1cc(Nc2nccc(-n3c(=O)oc4ccccc43)n2)c(OC)cc1N(C)CCN(C)C]

The title compound was prepared from 3-(2-(4-((2-(dimethylamino)ethyl)(methyl) amino)-2-methoxy-5-nitrophenylamino)pyrimidin-4-yl)benzo[d]oxazol-2(3H)-one by a method similar to those described in Steps 6 and 7 of Example 1.

$^1$H NMR (CDCl$_3$): δ 12.21 (1H, br), 9.51 (1H, br), 9.22 (1H, s), 8.55 (1H, d, J=5.6 Hz), 8.25 (1H, d, J=8.0 Hz), 7.51 (1H, s), 7.26 (1H, s), 7.23-7.16 (4H, m), 6.72 (1H, s), 6.31 (1H, dd, J=2.0 Hz, 16.8 Hz), 5.67 (1H, dd, J=2.0 Hz, 10.4 Hz), 3.90 (3H, s), 3.29 (2H, br), 3.13 (2H, br), 2.76 (9H, br).

Example 6: N-(2-((2-hydroxyethyl)(methyl)amino)-4-methoxy-5-(4-(3-methyl-2-oxo-2,3-dihydro-1H-benzo[d]imidazol-1-yl)pyrimidin-2-ylamino)phenyl)acrylamide

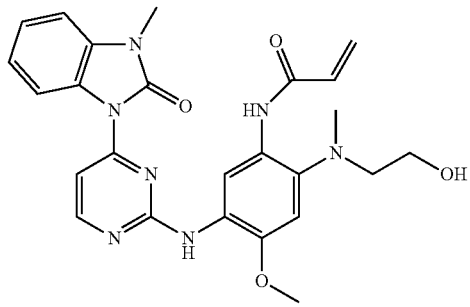 [SMILES: C=CC(=O)Nc1cc(Nc2nccc(-n3c(=O)n(C)c4ccccc43)n2)c(OC)cc1N(C)CCO]

Step 1: 1-(2-(4-((2-hydroxyethyl)(methyl)amino)-2-methoxy-5-nitrophenylamino) pyrimidin-4-yl)-3-methyl-1H-benzo[d]imidazol-2(3H)-one

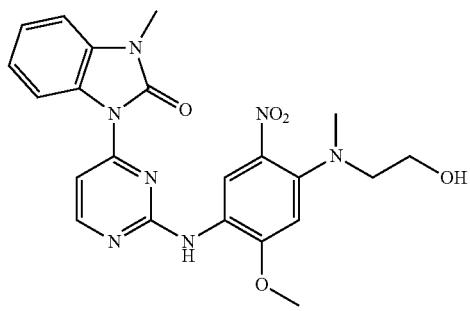 [SMILES: COc1cc(N(C)CCO)c([N+](=O)[O-])cc1Nc1nccc(-n2c(=O)n(C)c3ccccc32)n1]

The title compound was prepared from 2-(methylamino) ethanol by a method similar to that described in Step 5 of Example 1.

$^1$H NMR (CDCl$_3$): δ 8.97 (1H, s), 8.52 (1H, d, J=6.0 Hz), 8.26 (1H, J=7.2 Hz), 7.83 (1H, d, J=5.6 Hz), 7.56 (1H, s), 7.27-7.23 (1H, m), 7.18-7.16 (1H, m), 7.04 (1H, J=7.2 Hz), 6.70 (1H, s), 4.00 (3H, s), 3.79-3.76 (2H, m), 3.48 (3H, s), 3.40 (2H, t, J=7.2 Hz), 2.84 (3H, s).

Step 2: N-(2-((2-hydroxyethyl)(methyl)amino)-4-methoxy-5-(4-(3-methyl-2-oxo-2,3-dihydro-1H-benzo[d]imidazol-1-yl)pyrimidin-2-ylamino)phenyl)acrylamide

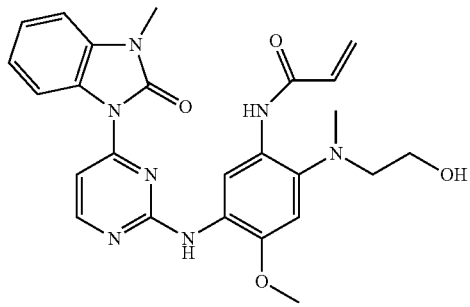 [SMILES: C=CC(=O)Nc1cc(Nc2nccc(-n3c(=O)n(C)c4ccccc43)n2)c(OC)cc1N(C)CCO]

The title compound was prepared from 1-(2-(4-((2-hydroxyethyl)(methyl)amino)-2-methoxy-5-nitrophenylamino)pyrimidin-4-yl)-3-methyl-1H-benzo[d]imidazol-2(3H)-one by a method similar to those described in Steps 6 and 7 of Example 1.

$^1$H NMR (CDCl$_3$): δ 9.30 (1H, s), 9.03 (1H, s), 8.52 (1H, d, J=5.6 Hz), 8.32 (1H, d, J=8.0 Hz), 7.80 (1H, d, J=5.6 Hz), 7.46 (1H, s), 7.18-7.14 (1H, m), 7.08-7.03 (1H, m), 7.01-6.95 (1H, m), 6.77 (1H, s), 6.34-6.32 (2H, m), 5.65-5.63 (1H, m), 3.87 (3H, s), 3.77-3.74 (2H, m), 3.45 (3H, s), 2.99 (2H, t, J=4.8 Hz), 3.75 (3H, s).

Example 7: (E)-N-(2-((2-(dimethylamino)ethyl)(methyl)amino)-4-methoxy-5-(4-(3-methyl-2-oxo-2,3-dihydro-1H-benzo[d]imidazol-1-yl)pyrimidin-2-ylamino)phenyl)-4-methoxybut-2-enamide

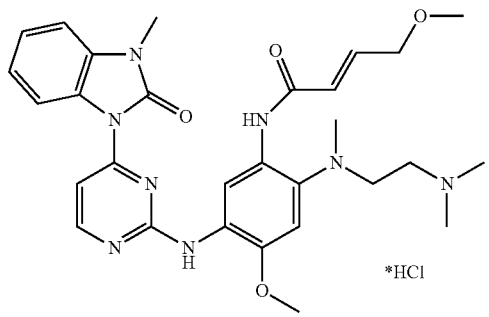 [SMILES: COC/C=C/C(=O)Nc1cc(Nc2nccc(-n3c(=O)n(C)c4ccccc43)n2)c(OC)cc1N(C)CCN(C)C]

The title compound was prepared from 1-(2-(5-amino-4-((2-(dimethylamino)ethyl) (methyl)amino)-2-methoxyphenylamino)pyrimidin-4-yl)-3-methyl-1H-benzo[d]imidazol-2(3H)-one and (E)-4-methoxybut-2-enoyl chloride by a method similar to that described in Step 7 of Example 1.

$^1$H NMR (CDCl$_3$): δ 12.32 (1H, br), 9.24 (1H, br), 9.17 (1H, br), 8.52 (1H, d, J=5.6 Hz), 8.31 (1H, d, J=8.0 Hz), 7.80 (1H, d, J=5.6 Hz), 7.49 (1H, br), 7.19-7.10 (2H, m), 6.99-6.96 (2H, m), 6.90-6.84 (1H, m), 6.72 (1H, s), 4.14 (2H, d, J=3.2 Hz), 3.90 (3H, s), 3.45 (3H, s), 3.40 (3H, s), 3.38-3.35 (2H, m), 3.12-3.08 (2H, m), 2.80 (6H, s), 2.74 (3H, s).

Example 8: N-(4-methoxy-5-(4-(3-methyl-2-oxo-2,3-dihydrobenzo[d]imidazol-1-yl) pyrimidin-2-ylamino)-2-morpholinophenyl)acrylamide

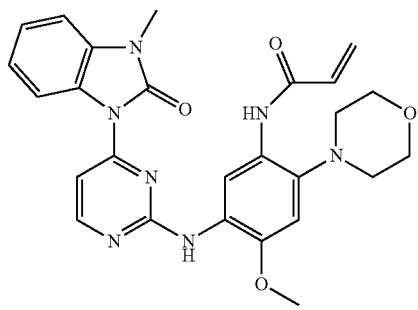 [SMILES: C=CC(=O)Nc1cc(Nc2nccc(-n3c(=O)n(C)c4ccccc43)n2)c(OC)cc1N1CCOCC1]

Step 1: 1-(2-(2-methoxy-4-morpholino-5-nitrophenylamino)pyrimidin-4-yl)-3-methyl-1H-benzo[d]imidazol-2(3H)-one

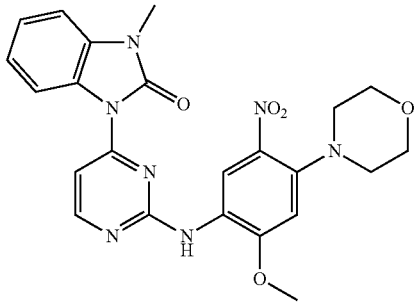 [SMILES: COc1cc(N2CCOCC2)c([N+](=O)[O-])cc1Nc1nccc(-n2c(=O)n(C)c3ccccc32)n1]

The title compound was prepared from 1-(2-(4-fluoro-2-methoxy-5-nitrophenylamino)pyrimidin-4-yl)-3-methyl-1H-benzo[d]imidazol-2(3H)-one p-toluenesulfonate and morpholine by a method similar to that described in Step 5 of Example 1.

$^1$H NMR (CDCl$_3$): δ 9.10 (1H, s), 8.54 (1H, d, J=5.6 Hz), 8.27 (1H, d, J=8.0 Hz), 7.85 (1H, d, J=5.6 Hz), 7.59 (1H, s), 7.27-7.24 (1H, m), 7.19-7.17 (1H, m), 7.05 (1H, d, J=8.0 Hz), 6.65 (1H, s), 4.04 (3H, s), 3.91-3.89 (4H, m), 3.49 (3H, s), 3.10-3.08 (4H, m).

Step 2: N-(4-methoxy-5-(4-(3-methyl-2-oxo-2,3-dihydrobenzo[d]imidazol-1-yl) pyrimidin-2-ylamino)-2-morpholinophenyl)acrylamide

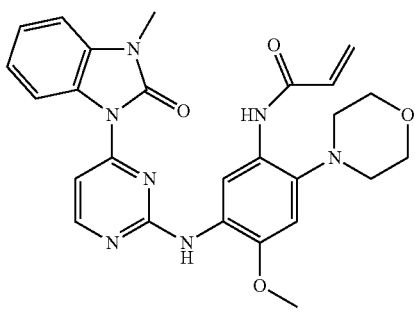 [SMILES: C=CC(=O)Nc1cc(Nc2nccc(-n3c(=O)n(C)c4ccccc43)n2)c(OC)cc1N1CCOCC1]

The title compound was prepared from 1-(2-(2-methoxy-4-morpholino-5-nitrophenylamino)pyrimidin-4-yl)-3-methyl-1H-benzo[d]imidazol-2(3H)-one by a method similar to those described in Steps 6 and 7 of Example 1.

$^1$H NMR (CDCl$_3$): δ 9.37 (1H, s), 8.55 (1H, d, J=5.6 Hz), 8.48 (1H, s), 8.34 (1H, d, J=8.0 Hz), 7.81 (1H, d, J=5.6 Hz), 7.46 (1H, s), 7.20-7.16 (1H, m), 7.10-7.06 (1H, m), 7.01-6.99 (1H, m), 6.79 (1H, s), 6.36-6.22 (2H, m), 5.75-5.72 (1H, m), 3.91-3.88 (7H, m), 3.46 (3H, s), 2.90 (4H, t, J=4.8 Hz).

Example 9: N-(2-((2-(dimethylamino)ethyl)(methyl)amino)-4-methoxy-5-(4-(5-methyl-2-oxo-2,3-dihydrobenzo[d]imidazol-1-yl)pyrimidin-2-ylamino)phenyl)acrylamide Hydrochloride

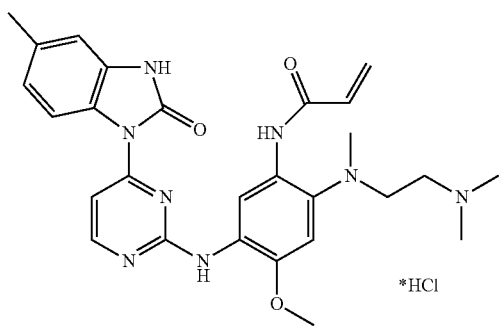

Step 1: N¹-(2-chloropyrimidin-4-yl)-4-methylbenzene-1,2-diamine

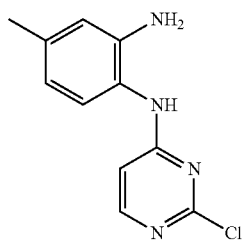 [SMILES: Cc1ccc(Nc2ccnc(Cl)n2)c(N)c1]

The title compound was prepared from 4-methylbenzene-1,2-diamine and 2,4-dichloropyrimidine by a method similar to that described in Step 1 of Example 1.

¹H NMR (CDCl$_3$): δ 8.06 (1H, d, J=6.0 Hz), 7.00 (1H, d, J=8.0 Hz), 6.77 (1H, s), 6.66 (1H, s), 6.62 (1H, d, J=8.0 Hz), 6.21 (1H, d, J=6.0 Hz), 3.79 (2H, br), 2.31 (3H, s).

Step 2: 1-(2-chloropyrimidin-4-yl)-5-methyl-1H-benzo[d]imidazol-2(3H)-one

The title compound was prepared from N¹-(2-chloropyrimidin-4-yl)-4-methylbenzene-1,2-diamine and carbonyldiimidazole by a method similar to that described in Step 2 of Example 1.

¹H NMR (CDCl$_3$): δ 8.62 (1H, d, J=5.6 Hz), 8.47 (1H, d, J=5.6 Hz), 8.34 (1H, d, J=8.4 Hz), 7.97 (1H, s), 7.03 (1H, d, J=8.4 Hz), 6.91 (1H, s), 2.42 (3H, s).

Step 3: 1-(2-(4-fluoro-2-methoxy-5-nitrophenylamino)pyrimidin-4-yl)-5-methyl-1H-benzo[d]imidazol-2(3H)-one p-toluenesulfonate

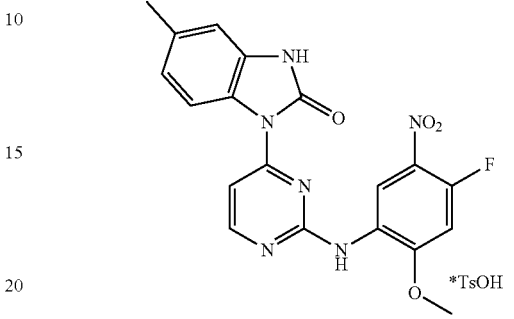

The title compound was prepared from 1-(2-chloropyrimidin-4-yl)-5-methyl-1H-benzo[d]imidazol-2(3H)-one and 4-fluoro-2-methoxy-5-nitroaniline by a method similar to that described in Step 4 of Example 1.

¹H NMR (DMSO-d$_6$): δ 11.39 (1H, s), 9.04 (1H, s), 8.61 (1H, d, J=8.4 Hz), 8.49 (1H, d, J=5.6 Hz), 8.04-8.02 (1H, m), 7.82 (1H, d, J=5.6 Hz), 7.49-7.41 (3H, m), 7.11 (2H, d, J=8.0 Hz), 6.93 (1H, s), 6.87 (1H, s), 6.76-6.74 (1H, m), 3.97 (3H, s), 2.33 (3H, s), 2.29 (3H, s).

Step 4: 1-(2-(4-((2-(dimethylamino)ethyl)(methyl)amino)-2-methoxy-5-nitrophenylamino)pyrimidin-4-yl)-5-methyl-1H-benzo[d]imidazol-2(3H)-one

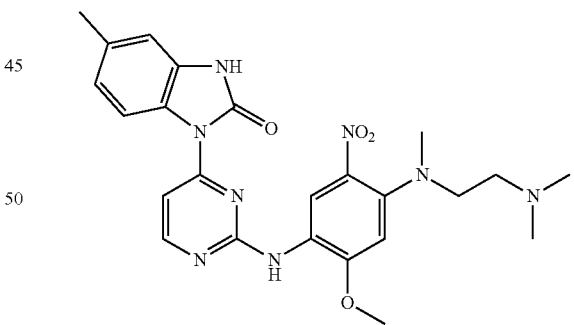

The title compound was prepared from 1-(2-(4-fluoro-2-methoxy-5-nitrophenylamino)pyrimidin-4-yl)-5-methyl-1H-benzo[d]imidazol-2(3H)-one p-toluenesulfonate and diisopropylethylamine by a method similar to that described in Step 5 of Example 1.

¹H NMR (CDCl$_3$): δ 8.92 (1H, s), 8.50 (1H, d, J=5.6 Hz), 8.30 (1H, br), 8.11 (1H, d, J=8.0 Hz), 7.78 (1H, d, J=5.6 Hz), 7.45 (1H, s), 6.94 (1H, d, J=8.0 Hz), 6.89 (1H, s), 6.70 (1H, s), 3.98 (3H, s), 3.31 (2H, t, J=6.8 Hz), 2.88 (3H, s), 2.61 (2H, t, J=6.8 Hz), 2.40 (3H, s), 2.31 (6H, s).

Step 5: N-(2-((2-(dimethylamino)ethyl)(methyl) amino)-4-methoxy-5-(4-(5-methyl-2-oxo-2,3-dihydrobenzo[d]imidazol-1-yl)pyrimidin-2-ylamino)phenyl)acrylamide Hydrochloride

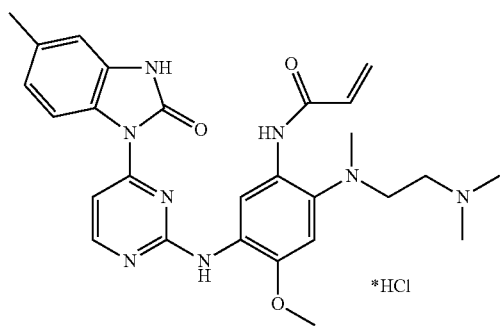

The title compound was prepared from 1-(2-(4-((2-(dimethylamino)ethyl)(methyl) amino)-2-methoxy-5-nitrophenylamino)pyrimidin-4-yl)-5-methyl-1H-benzo[d]imidazol-2(3H)-one by a method similar to those described in Steps 6 and 7 of Example 1.

$^1$H NMR (MeOD): δ 8.32 (1H, d, J=6.0 Hz), 7.91 (1H, d, J=8.0 Hz), 7.61 (1H, d, J=5.6 Hz), 6.87-6.84 (2H, m), 6.78 (1H, s), 6.70 (1H, d, J=8.0 Hz), 6.40-6.26 (2H, m), 5.73-5.70 (1H, m), 3.86 (3H, s), 3.26 (2H, br), 2.93 (2H, br), 2.61 (3H, s), 2.59 (6H, s), 2.22 (3H, s).

Example 10: N-(2-((2-(dimethylamino)ethyl)(methyl)amino)-5-(4-(5-fluoro-3-methyl-2-oxo-2,3-dihydrobenzo[d]imidazol-1-yl)pyrimidin-2-ylamino)-4-methoxyphenyl) acrylamide Hydrochloride

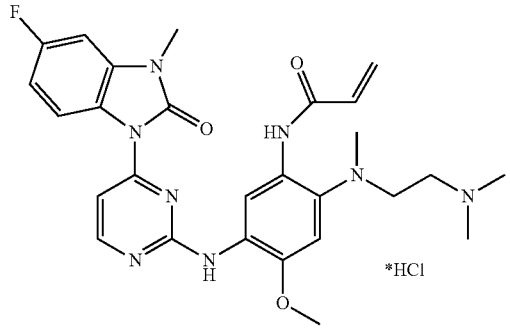 [SMILES: C=CC(=O)Nc1cc(Nc2nccc(-n3c(=O)n(C)c4cc(F)ccc43)n2)c(OC)cc1N(C)CCN(C)C]

Step 1: N$^1$-(2-dichloropyrimidin-4-yl)-4-fluorobenzene-1,2-diamine

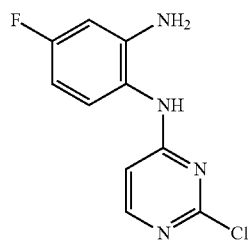 [SMILES: Nc1cc(F)ccc1Nc1ccnc(Cl)n1]

The title compound was prepared from 2,4-dichloropyrimidine and 4-fluorobenzene-1,2-diamine by a method similar to that described in Step 1 of Example 1.

$^1$H NMR (CDCl$_3$): δ 8.06 (1H, d, J=6.0 Hz), 7.06-7.03 (1H, m), 6.71 (1H, s), 6.52-6.44 (2H, m), 6.14 (1H, d, J=6.0 Hz), 3.94 (2H, br).

Step 2: 1-(2-chloropyrimidin-4-yl)-5-fluoro-1H-benzo[d]imidazol-2(3H)-one

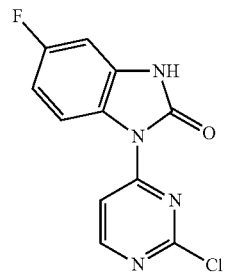 [SMILES: O=c1[nH]c2cc(F)ccc2n1-c1ccnc(Cl)n1]

The title compound was prepared from N$^1$-(2-dichloropyrimidin-4-yl)-4-fluorobenzene-1,2-diamine and carbonyldiimidazole by a method similar to that described in Step 2 of Example 1.

$^1$H NMR (DMSO-d$_6$): δ 11.81 (1H, s), 8.77 (1H, d, J=6.0 Hz), 8.40 (1H, d, J=6.0 Hz), 8.24-8.21 (1H, m), 7.03-6.96 (2H, m).

Step 3: 1-(2-chloropyrimidin-4-yl)-5-fluoro-3-methyl-1H-benzo[d]imidazol-2(3H)-one

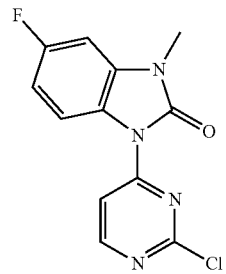 [SMILES: Cn1c(=O)n(-c2ccnc(Cl)n2)c2ccc(F)cc21]

The title compound was prepared from 1-(2-chloropyrimidin-4-yl)-5-fluoro-1H-benzo[d]imidazol-2(3H)-one by a method similar to that described in Step 3 of Example 1.

$^1$H NMR (DMSO-d$_6$): δ 8.77 (1H, d, J=5.6 Hz), 8.38 (1H, d, J=5.6 Hz), 8.23-8.19 (1H, m), 7.29 (1H, d, J=8.8 Hz), 7.04-7.00 (1H, m), 3.36 (3H, s).

Step 4: 5-fluoro-1-(2-(4-fluoro-2-methoxy-5-nitrophenylamino)pyrimidin-4-yl)-3-methyl-1H-benzo[d]imidazol-2(3H)-one p-toluenesulfonate

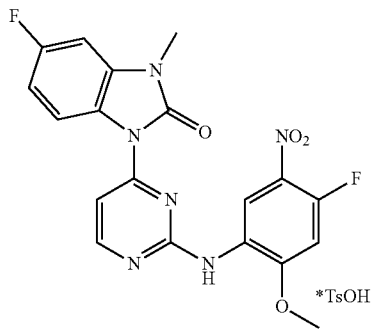 [SMILES: COc1cc(F)c([N+](=O)[O-])cc1Nc1nccc(-n2c(=O)n(C)c3cc(F)ccc32)n1]

The title compound was prepared from 1-(2-chloropyrimidin-4-yl)-5-fluoro-3-methyl-1H-benzo[d]imidazol-2(3H)-one and 4-fluoro-2-methoxy-5-nitroaniline by a method similar to that described in Step 4 of Example 1, and was directly used in the next reaction step.

Step 5: 1-(2-(4-((2-(dimethylamino)ethyl)(methyl)amino)-2-methoxy-5-nitrophenylamino)pyrimidin-4-yl)-5-fluoro-3-methyl-1H-benzo[d]imidazol-2(3H)-one

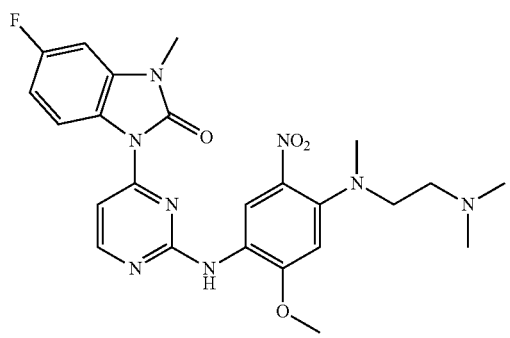 [SMILES: COc1cc(N(C)CCN(C)C)c([N+](=O)[O-])cc1Nc1nccc(-n2c(=O)n(C)c3cc(F)ccc32)n1]

The title compound was prepared from 5-fluoro-1-(2-(4-fluoro-2-methoxy-5-nitrophenylamino)pyrimidin-4-yl)-3-methyl-1H-benzo[d]imidazol-2(3H)-one p-toluenesulfonate by a method similar to that described in Step 5 of Example 1.

$^1$H NMR (CDCl$_3$): δ 8.86 (1H, s), 8.50 (1H, d, J=5.6 Hz), 8.24-8.21 (1H, m), 7.81 (1H, d, J=5.6 Hz), 7.42 (1H, s), 6.86-6.81 (1H, m), 6.76 (1H, dd, J=2.8 Hz, 8.0 Hz), 6.69 (1H, s), 3.98 (3H, s), 3.44 (3H, s), 3.29 (2H, t, J=7.2 Hz), 2.89 (3H, s), 2.57 (2H, t, J=7.2 Hz), 2.27 (6H, s).

Step 6: N-(2-((2-(dimethylamino)ethyl)(methyl)amino)-5-(4-(5-fluoro-3-methyl-2-oxo-2,3-dihydrobenzo[d]imidazol-1-yl)pyrimidin-2-ylamino)-4-methoxyphenyl) acrylamide Hydrochloride

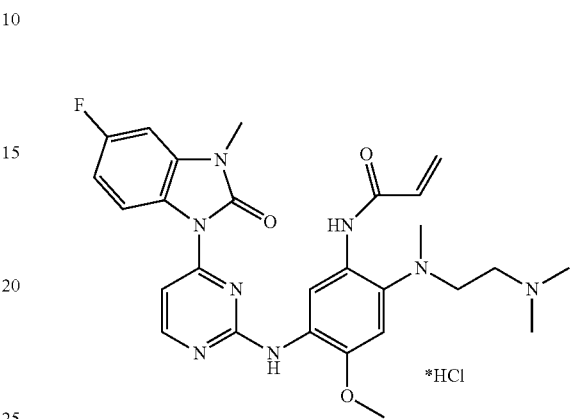

The title compound was prepared from 1-(2-(4-((2-(dimethylamino)ethyl)(methyl) amino)-2-methoxy-5-nitrophenylamino)pyrimidin-4-yl)-5-fluoro-3-methyl-1H-benzo[d]imidazol-2(3H)-one by a method similar to those described in Steps 6 and 7 of Example 1.

$^1$H NMR (DMSO-d$_6$): δ 10.26 (1H, s), 9.78 (1H, s), 8.74 (1H, s), 8.43 (1H, d, J=6.0 Hz), 8.17 (2H, s), 7.70 (1H, d, J=6.0 Hz), 7.22 (1H, dd, J=2.4 Hz, 8.8 Hz), 7.06-6.99 (1H, m), 6.97 (1H, s), 6.79-6.75 (1H, m), 6.21 (1H, dd, J=2.0 Hz, 16.8 Hz), 5.71-5.68 (1H, m), 3.80 (3H, s), 3.63-3.57 (2H, m), 3.34 (3H, s), 3.16-3.09 (2H, m), 2.75 (6H, s), 2.63 (3H, s).

Example 11: N-(2-((2-(dimethylamino)ethyl)(methyl)amino)-5-(4-(5-fluoro-2-oxo-2,3-dihydrobenzo[d]imidazol-1-yl)pyrimidin-2-ylamino)-4-methoxyphenyl)acrylamide Hydrochloride

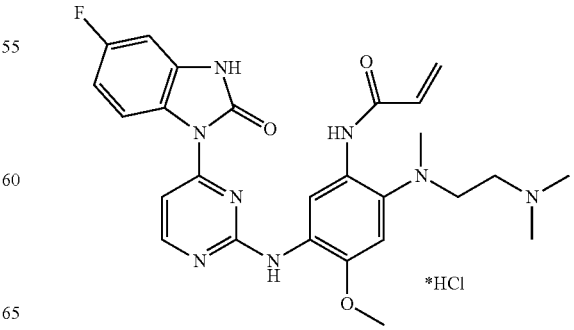

Step 1: 5-fluoro-1-(2-(4-fluoro-2-methoxy-5-nitrophenylamino)pyrimidin-4-yl)-1H-benzo[d]imidazol-2(3H)-one p-toluenesulfonate Step 3: N-(2-((2-(dimethylamino)ethyl)(methyl)amino)-5-(4-(5-fluoro-2-oxo-2,3-dihydrobenzo[d]imidazol-1-yl)pyrimidin-2-ylamino)-4-methoxyphenyl)acrylamide Hydrochloride

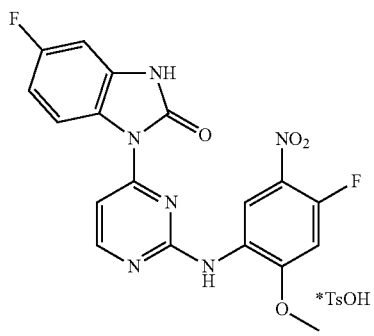

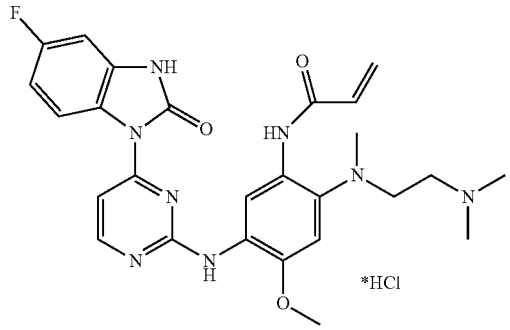 [SMILES: C=CC(=O)Nc1cc(Nc2nccc(-n3c(=O)[nH]c4cc(F)ccc43)n2)c(OC)cc1N(C)CCN(C)C]

The title compound was prepared from 1-(2-chloropyrimidin-4-yl)-5-fluoro-1H-benzo[d]imidazol-2(3H)-one and 4-fluoro-2-methoxy-5-nitroaniline by a method similar to that described in Step 4 of Example 1.

$^1$H NMR (DMSO-$d_6$): δ 11.68 (1H, s), 9.24 (1H, s), 8.64 (1H, d, J=8.0 Hz), 8.51 (1H, d, J=6.0 Hz), 8.23 (1H, br), 7.83 (1H, d, J=6.0 Hz), 7.48 (2H, d, J=8.0 Hz), 7.43 (1H, d, J=8.0 Hz), 7.12 (2H, d, J=8.0 Hz), 6.94-6.91 (1H, m), 6.80-6.75 (1H, m), 3.98 (3H, s), 2.29 (3H, s).

Step 2: 1-(2-(4-((2-(dimethylamino)ethyl)(methyl)amino)-2-methoxy-5-nitrophenylamino)pyrimidin-4-yl)-5-fluoro-1H-benzo[d]imidazol-2(3H)-one The title compound was prepared from 1-(2-(4-((2-(dimethylamino)ethyl)(methyl)amino)-2-methoxy-5-nitrophenylamino)pyrimidin-4-yl)-5-fluoro-1H-benzo[d]imidazol-2(3H)-one by a method similar to those described in Steps 6 and 7 of Example 1.

$^1$H NMR (CD$_3$OD): δ 8.45 (1H, dd, J=2.4 Hz, 5.6 Hz), 8.17-8.12 (1H, m), 7.73-7.69 (2H, m), 7.22 (1H, d, J=8.0 Hz), 6.95 (1H, d, J=3.6 Hz), 6.88-6.83 (1H, m), 6.77-6.71 (1H, m), 6.44-6.42 (1H, m), 5.84-5.81 (1H, m), 3.97 (3H, s), 3.49-3.46 (2H, m), 3.23 (2H, m), 2.84 (6H, s), 2.71 (3H, s).

Example 12: N-(4-methoxy-2-(methyl(2-(methylamino)ethyl)amino)-5-(4-(3-methyl-2-oxo-2,3-dihydrobenzo[d]imidazol-1-yl)pyrimidin-2-ylamino)phenyl)acrylamide Hydrochloride

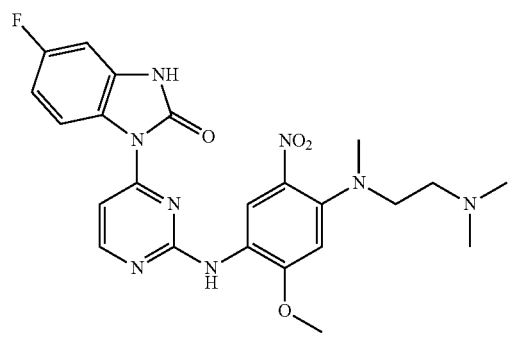 [SMILES: COc1cc(N(C)CCN(C)C)c([N+](=O)[O-])cc1Nc1nccc(-n2c(=O)[nH]c3cc(F)ccc32)n1]

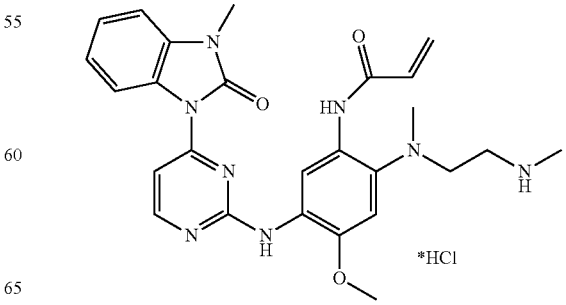

The title compound was prepared from 5-fluoro-1-(2-(4-fluoro-2-methoxy-5-nitrophenylamino)pyrimidin-4-yl)-1H-benzo[d]imidazol-2(3H)-one p-toluenesulfonate by a method similar to that described in Step 5 of Example 1.

$^1$H NMR (DMSO-$d_6$): δ 8.83 (1H, s), 8.47 (1H, d, J=5.6 Hz), 8.26 (1H, s), 8.23-8.17 (1H, m), 7.77-7.68 (2H, m), 6.99-6.94 (2H, m), 6.77-6.72 (1H, m), 3.99 (3H, s), 3.63 (2H, m), 3.19-3.15 (2H, m), 2.88 (3H, s), 2.66 (6H, s).

Step 1: tert-butyl 2-((5-methoxy-4-(4-(3-methyl-2-oxo-2,3-dihydrobenzo[d]imidazol-1-yl)pyrimidin-2-ylamino)-2-nitrophenyl)(methyl)amino)ethyl(methyl)carbamate

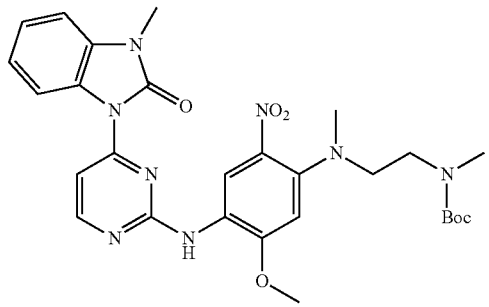 [SMILES: COc1cc(N(C)CCN(C)C(=O)OC(C)(C)C)c([N+](=O)[O-])cc1Nc1nccc(-n2c(=O)n(C)c3ccccc32)n1]

The title compound was prepared from 1-(2-(4-fluoro-2-methoxy-5-nitrophenylamino)pyrimidin-4-yl)-3-methyl-1H-benzo[d]imidazol-2(3H)-one p-toluenesulfonate and tert-butyl 2-(methylamino)ethylcarbamate by a method similar to that described in Step 5 of Example 1.

$^1$H NMR (CDCl$_3$): δ 8.94 (1H, s), 8.51 (1H, d, J=5.6 Hz), 8.26 (1H, d, J=7.2 Hz), 7.80 (1H, d, J=5.6 Hz), 7.48 (1H, s), 7.24-7.22 (1H, m), 7.17-7.15 (1H, m), 7.03 (1H, d, J=7.2 Hz), 6.76 (1H, s), 4.01 (3H, s), 3.47-3.37 (5H, m), 3.31-3.23 (2H, m), 2.91 (3H, s), 2.83 (3H, s), 1.44 (9H, s).

Step 2: tert-butyl 2-((2-acrylamido-5-methoxy-4-(4-(3-methyl-2-oxo-2,3-dihydrobenzo[d]imidazol-1-yl)pyrimidin-2-ylamino)phenyl)(methyl)amino)ethyl (methyl) carbamate

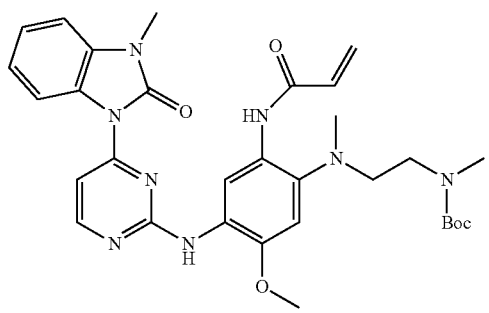 [SMILES: C=CC(=O)Nc1cc(Nc2nccc(-n3c(=O)n(C)c4ccccc43)n2)c(OC)cc1N(C)CCN(C)C(=O)OC(C)(C)C]

The title compound was prepared from tert-butyl 2-((5-methoxy-4-(4-(3-methyl-2-oxo-2,3-dihydrobenzo[d]imidazol-1-yl)pyrimidin-2-ylamino)-2-nitrophenyl)(methyl) amino) ethyl(methyl) carbamate by a method similar to those described in Steps 6 and 7 of Example 1.

$^1$H NMR (CDCl$_3$): δ 9.37 (1H, br), 8.67 (1H, br), 8.54 (1H, d, J=5.6 Hz), 8.34 (1H, d, J=7.6 Hz), 7.79 (1H, d, J=5.6 Hz), 7.43 (1H, s), 7.19-7.15 (1H, m), 7.08-7.04 (1H, m), 6.98 (1H, d, J=7.6 Hz), 6.79 (1H, s), 6.35 (2H, d, J=2.4 Hz), 5.69-5.72 (1H, m), 3.89 (3H, s), 3.45 (3H, s), 3.40-3.37 (2H, m), 3.00-2.85 (2H, m), 2.85 (3H, s), 2.70 (3H, s), 1.47 (9H, s).

Step 3: N-(4-methoxy-2-(methyl(2-(methylamino) ethyl)amino)-5-(4-(3-methyl-2-oxo-2,3-dihydrobenzo[d]imidazol-1-yl)pyrimidin-2-ylamino)phenyl)acrylamide Hydrochloride

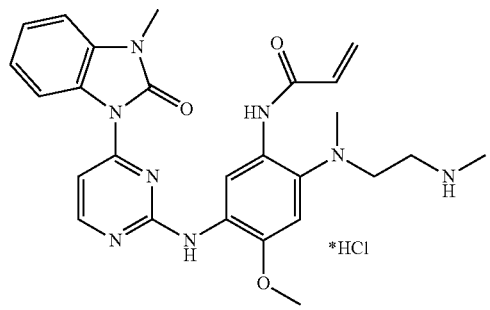 [SMILES: C=CC(=O)Nc1cc(Nc2nccc(-n3c(=O)n(C)c4ccccc43)n2)c(OC)cc1N(C)CCNC]

Acetyl chloride (0.3 mL, 1.7 mmol) was slowly added dropwise to anhydrous methanol (3 mL) cooled with an external ice-water bath and stirring was continued for 1 hour. tert-butyl 2-((2-acrylamido-5-methoxy-4-(4-(3-methyl-2-oxo-2,3-dihydrobenzo[d]imidazol-1-yl) pyrimidin-2-ylamino)phenyl)(methyl)amino)ethyl(methyl)carbamate (100 mg, 0.166 mmol) was dispersed in anhydrous methanol (2 mL) and then added into the above solution of hydrogen chloride in methanol. The system was allowed to naturally warm to room temperature and stirred overnight, and then concentrated under vacuum to remove the solvent. Silica gel column chromatography (DCM:MeOH=20:1) was conducted to give the title compound (78 mg, 93%).

$^1$H NMR (CD$_3$OD): δ 8.45 (1H, d, J=5.6 Hz), 8.19 (2H, d, J=6.0 Hz), 7.77 (1H, d, J=5.6 Hz), 7.21-7.16 (2H, m), 7.09-7.05 (1H, m), 6.95 (1H, s), 6.50-6.36 (2H, m), 5.80 (1H, dd, J=2.0 Hz, 6.0 Hz), 3.96 (3H, s), 3.45 (3H, s), 3.35 (4H, br), 2.73 (3H, s), 2.72 (3H, s).

Example 13: N-(2-((2-(dimethylamino)ethyl) (methyl)amino)-4-methoxy-5-(4-(3-methyl-2-oxo-2,3-dihydro-1H-benzo[d]imidazol-1-yl)pyrimidin-2-ylamino)phenyl)acrylamide

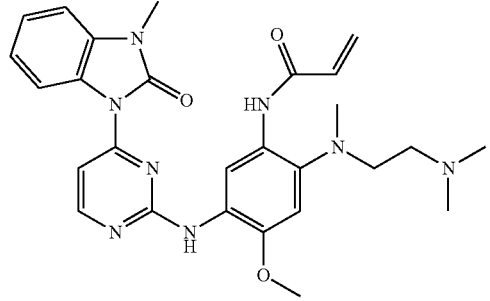 [SMILES: C=CC(=O)Nc1cc(Nc2nccc(-n3c(=O)n(C)c4ccccc43)n2)c(OC)cc1N(C)CCN(C)C]

1-(2-(5-Amino-4-((2-(dimethylamino)ethyl)(methyl) amino)-2-methoxyphenylamino) pyrimidin-4-yl)-3-methyl-1H-benzo[d]imidazol-2(3H)-one (82 g) obtained in Step 6 of Example 1 was added into THF (800 mL) and water (80 mL), and the mixture was stirred to dissolve. 3-Chloropropionyl chloride (24.8 g) was added dropwise thereto. After TLC showed the disappearance of the starting material, triethylamine (358.2 g) was added and the reaction system was heated to 65° C. After the reaction was completed, the reaction solution was concentrated to dryness and the residue was dissolved in 1 L of dichloromethane, and then separated twice with water (500 mL). The organic phases were collected and concentrated to give 88 g of a crude product. The resulting crude product was separated by column chromatography (DCM:MeOH=20:1) to give 62.5 g of the title compound.

ESI-MS [M+H]$^+$: 517.2677.

$^1$H NMR (DMSO-d$_6$): δ 10.05 (1H, s), 8.67 (1H, s), 8.5 (1H, s), 8.44 (1H, d, J=5.6 Hz), 8.12 (1H, d, J=7.6 Hz), 7.13 (2H, m), 6.9 (1H, t, J=6.4 Hz), 7.7 (1H, d, J=5.6 Hz), 7.05 (1H, s), 6.4 (1H, dd, J=10.15 Hz, 16.9 Hz), 6.21 (1H, dd, J=1.6 Hz, 16.9 Hz), 5.72 (1H, brd, J=11.50 Hz), 3.77 (3H, s), 3.35 (3H, s), 2.91 (2H, t, J=5.65 Hz), 2.75 (3H, s), 2.34 (2H, t, J=5.7 Hz), 2.21 (6H, s).

Example 14: N-(5-(4-(5-chloro-3-methyl-2-oxo-2,3-dihydro-1H-benzo[d]imidazole-1-yl)pyrimidin-2-ylamino)-2-((2-(dimethylamino)ethyl)(methyl)amino)-4-methoxyphenyl) acrylamide Hydrochloride

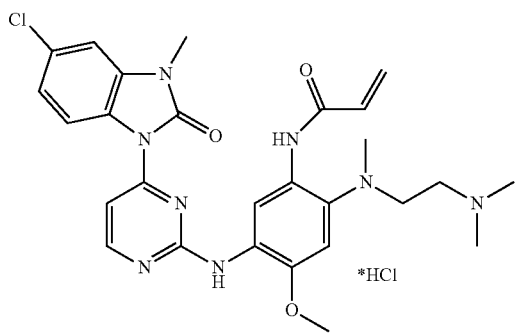 [SMILES: C=CC(=O)Nc1cc(Nc2nccc(-n3c(=O)n(C)c4cc(Cl)ccc43)n2)c(OC)cc1N(C)CCN(C)C]

Step 1: 4-chloro-N$^1$-(2-chloropyrimidin-4-yl)benzene-1,2-diamine

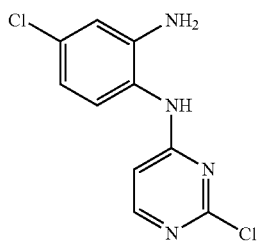 [SMILES: Nc1cc(Cl)ccc1Nc1ccnc(Cl)n1]

The title compound was prepared from 2,4-dichloropyrimidine and 4-chloro-1,2-phenylenediamine by a method similar to that described in Step 1 of Example 1.

$^1$H NMR (DMSO-d$_6$): δ 9.14 (1H, s), 8.05 (1H, d, J=6.0 Hz), 7.06 (1H, d, J=8.4 Hz), 6.80 (1H, s), 6.56 (1H, dd, J=2.8 Hz, 8.0 Hz), 6.35 (1H, s), 5.32 (2H, br s).

Step 2: 5-chloro-1-(2-chloropyrimidin-4-yl)-1H-benzo[d]imidazol-2(3H)-one

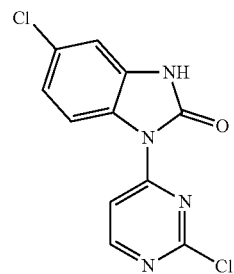 [SMILES: O=c1[nH]c2cc(Cl)ccc2n1-c1ccnc(Cl)n1]

The title compound was prepared from 4-chloro-N$^1$-(2-chloropyrimidin-4-yl) benzene-1,2-diamine and N,N'-carbonyldiimidazole by a method similar to that described in Step 2 of Example 1.

$^1$H NMR (DMSO-d$_6$): δ 11.79 (1H, br s), 8.79 (1H, d, J=5.6 Hz), 8.39 (1H, d, J=6.0 Hz), 8.21 (1H, d, J=8.8 Hz), 7.23 (1H, dd, J=2.0 Hz, 8.4 Hz), 7.12 (1H, s).

Step 3: 5-chloro-1-(2-chloropyrimidin-4-yl)-3-methyl-1H-benzo[d]imidazol-2(3H)-one

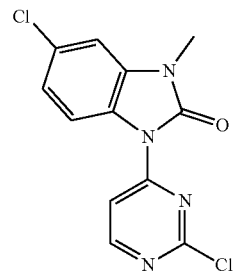 [SMILES: Cn1c(=O)n(-c2ccnc(Cl)n2)c2ccc(Cl)cc21]

The title compound was prepared from 5-chloro-1-(2-chloropyrimidin-4-yl)-1H-benzo[d]imidazol-2(3H)-one by a method similar to that described in Step 3 of Example 1.

$^1$H NMR (DMSO-d$_6$): δ 8.78 (1H, d, J=5.6 Hz), 8.38 (1H, d, J=5.6 Hz), 8.19 (1H, d, J=8.8 Hz), 7.45 (1H, s), 7.23 (1H, d, J=8.8 Hz), 3.36 (3H, s).

Step 4: 5-chloro-1-(2-(4-fluoro-2-methoxy-5-nitrophenylamino)pyrimidin-4-yl)-3-methyl-1H-benzo[d]imidazol-2(3H)-one

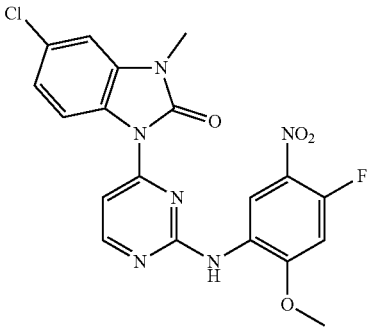 [SMILES: COc1cc(F)c([N+](=O)[O-])cc1Nc1nccc(-n2c(=O)n(C)c3cc(Cl)ccc32)n1]

The title compound was prepared from 5-chloro-1-(2-chloropyrimidin-4-yl)-3-methyl-1H-benzo[d]imidazol-2(3H)-one and 4-fluoro-2-methoxy-5-nitroaniline by a method similar to that described in Step 4 of Example 1.

$^1$H NMR (DMSO-d$_6$): 9.23 (1H, s), 8.61 (1H, d, J=8.0 Hz), 8.54 (1H, d, J=5.6 Hz), 8.22 (1H, d, J=8.0 Hz), 7.82 (1H, d, J=5.6 Hz), 7.44-7.41 (2H, m), 7.02 (1H, dd, J=2.0 Hz, 8.4 Hz), 3.97 (3H, s), 3.37 (3H, s).

Step 5: 5-chloro-1-(2-(4-((2-(dimethylamino)ethyl)(methyl)amino)-2-methoxy-5-nitrophenylamino)pyrimidin-4-yl)-3-methyl-1H-benzo[d]imidazol-2(3H)-one

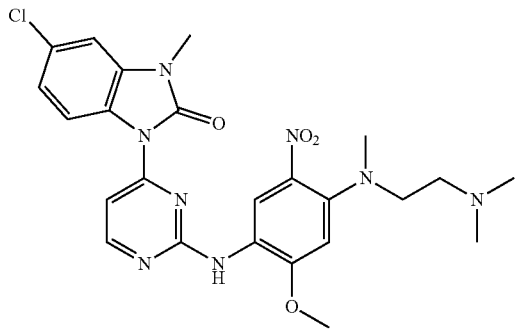

The title compound was prepared from 5-chloro-1-(2-(4-fluoro-2-methoxy-5-nitrophenylamino)pyrimidin-4-yl)-3-methyl-1H-benzo[d]imidazol-2(3H)-one by a method similar to that described in Step 5 of Example 1.

$^1$H NMR (CDCl$_3$): δ 8.84 (1H, s), 8.49 (1H, d, J=5.6 Hz), 8.19 (1H, d, J=8.4 Hz), 7.79 (1H, d, J=5.6 Hz), 7.42 (1H, s), 7.09 (1H, dd, J=2.4 Hz, 8.8 Hz), 7.00 (1H, s), 6.69 (1H, s), 3.98 (3H, s), 3.43 (3H, s) 3.29 (2H, t, J=7.2 Hz), 2.89 (3H, s), 2.56 (2H, t, J=7.2 Hz), 2.27 (6H, s).

Step 6: 1-(2-(5-amino-4-((2-(dimethylamino)ethyl)(methyl)amino)-2-methoxyphenylamino)pyrimidin-4-yl)-5-chloro-3-methyl-1H-benzo[d]imidazol-2(3H)-one

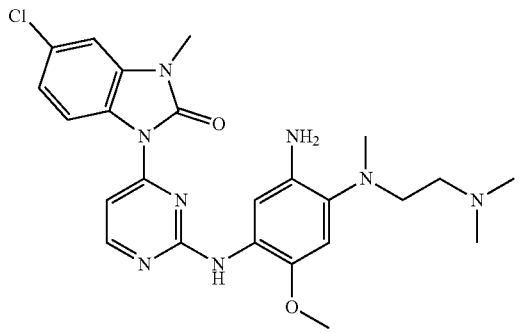 [SMILES: COc1cc(N(C)CCN(C)C)c([N+](=O)[O-])cc1Nc1nccc(-n2c(=O)n(C)c3cc(Cl)ccc32)n1]

5-Chloro-1-(2-(4-((2-(dimethylamino)ethyl)(methyl)amino)-2-methoxy-5-nitrophenylamino)pyrimidin-4-yl)-3-methyl-1H-benzo[d]imidazol-2(3H)-one (1.00 g) and zinc powder (1.24 g, 18.97 mmol) were dispersed in a mixed solution of dichloromethane/methanol (15 mL/15 mL). 20 mL of saturated ammonium chloride solution was added dropwise at room temperature, and the resulting mixture was stirred for 10 minutes and then filtered. To the filtrate was added water (30 mL) and the resulting mixture was extracted with dichloromethane (30 mL*3). The resulting organic phase was washed with saturated brine and concentrated under vacuum to remove the solvent to give the title compound, which was directly used in the next reaction step.

Step 7: N-(5-(4-(5-chloro-3-methyl-2-oxo-2,3-dihydro-1H-benzo[d]imidazole-1-yl)pyrimidin-2-ylamino)-2-((2-(dimethylamino)ethyl)(methyl)amino)-4-methoxyphenyl) acrylamide Hydrochloride

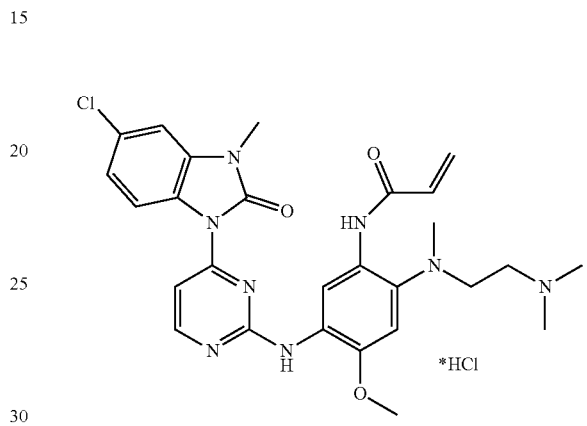

The title compound was prepared from 1-(2-(5-amino-4-((2-(dimethylamino)ethyl) (methyl)amino)-2-methoxyphenylamino)pyrimidin-4-yl)-5-chloro-3-methyl-1H-benzo[d]imidazol-2(3H)-one by a method similar to that described in Step 7 of Example 1.

$^1$H NMR (DMSO-d$_6$): δ 10.42 (1H, br s), 9.82 (1H, s), 8.78 (1H, s), 8.44 (1H, d, J=5.6 Hz), 8.18 (1H, s), 8.13 (1H, s), 7.66 (1H, d, J=5.6 Hz), 7.38 (1H, d, J=2.4 Hz), 7.13-7.06 (1H, m), 6.99-6.96 (2H, m), 6.20 (1H, dd, J=2.0 Hz, 16.8 Hz), 5.69 (1H, dd, J=2.0 Hz, 10.0 Hz), 3.80 (3H, s), 3.36-3.30 (7H, m), 2.75 (6H, s), 2.63 (3H, s).

Example 15: N-(5-(4-(5-bromo-3-methyl-2-oxo-2,3-dihydro-1H-benzo[d]imidazole-1-yl)pyrimidin-2-ylamino)-2-((2-(dimethylamino)ethyl)(methyl)amino)-4-methoxyphenyl) acrylamide Hydrochloride

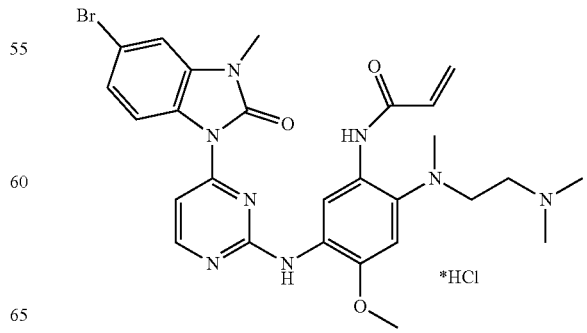

Step 1: 4-bromo-N¹-(2-chloropyrimidin-4-yl)benzene-1,2-diamine

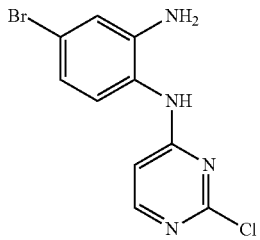 [SMILES: Nc1cc(Br)ccc1Nc1ccnc(Cl)n1]

The title compound was prepared from 2,4-dichloropyrimidine and 4-bromo-1,2-phenylenediamine by a method similar to that described in Step 1 of Example 1.

¹H NMR (DMSO-$d_6$): δ 9.13 (1H, s), 8.05 (1H, d, J=6.0 Hz), 7.01 (1H, d, J=8.8 Hz), 6.94 (1H, d, J=2.4 Hz), 6.69 (1H, dd, J=2.0 Hz, 8.4 Hz), 6.38 (1H, s), 5.31 (2H, br s).

Step 2: 5-bromo-1-(2-chloropyrimidin-4-yl)-1H-benzo[d]imidazol-2(3H)-one

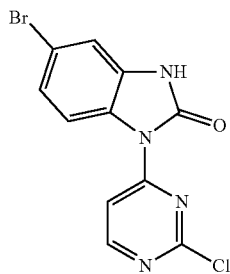

The title compound was prepared from 4-bromo-N¹-(2-chloropyrimidin-4-yl) benzene-1,2-diamine and N,N'-carbonyldiimidazole by a method similar to that described in Step 2 of Example 1.

¹H NMR (DMSO-$d_6$): δ 11.81 (1H, br s), 8.79 (1H, d, J=5.6 Hz), 8.40 (1H, d, J=5.6 Hz), 8.17 (1H, d, J=8.8 Hz), 7.37 (1H, dd, J=2.0 Hz, 8.8 Hz), 7.26 (1H, d, J=2.0 Hz).

Step 3: 5-bromo-1-(2-chloropyrimidin-4-yl)-3-methyl-1H-benzo[d]imidazol-2(3H)-one

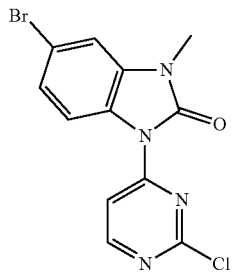

The title compound was prepared from 5-bromo-1-(2-chloropyrimidin-4-yl)-1H-benzo[d]imidazol-2(3H)-one by a method similar to that described in Step 3 of Example 1.

¹H NMR (DMSO-$d_6$): δ 8.81 (1H, d, J=6.0 Hz), 8.42 (1H, d, J=8.0 Hz), 8.19 (1H, d, J=8.4 Hz), 7.60 (1H, d, J=2.0 Hz), 7.41 (1H, dd, J=2.0 Hz, 8.4 Hz), 3.40 (3H, s).

Step 4: 5-bromo-1-(2-(4-fluoro-2-methoxy-5-nitrophenylamino)pyrimidin-4-yl)-3-methyl-1H-benzo[d]imidazol-2(3H)-one

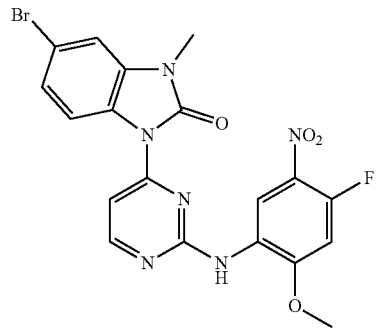

The title compound was prepared from 5-bromo-1-(2-chloropyrimidin-4-yl)-3-methyl-1H-benzo[d]imidazol-2(3H)-one and 4-fluoro-2-methoxy-5-nitroaniline by a method similar to that described in Step 4 of Example 1.

¹H NMR (DMSO-$d_6$): 9.22 (1H, s), 8.61 (1H, d, J=8.4 Hz), 8.54 (1H, d, J=5.6 Hz), 8.17 (1H, d, J =8.0 Hz), 7.82 (1H, d, J =5.6 Hz), 7.53 (1H, d, J=2.0 Hz), 7.43 (1H, d, J =13.2 Hz), 7.44-7.41 (2H, m), 7.14 (1H, dd, J=2.0 Hz, 13.2 Hz), 3.97 (3H, s), 3.37 (3H, s).

Step 5: 5-bromo-1-(2-(4-((2-(dimethylamino)ethyl)(methyl)amino)-2-methoxy-5-nitrophenylamino)pyrimidin-4-yl)-3-methyl-1H-benzo[d]imidazol-2(3H)-one

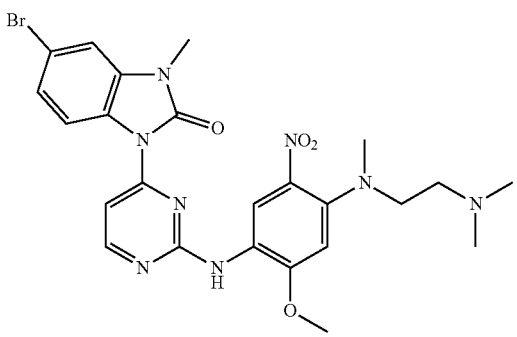

The title compound was prepared from 5-bromo-1-(2-(4-fluoro-2-methoxy-5-nitrophenylamino)pyrimidin-4-yl)-3-methyl-1H-benzo[d]imidazol-2(3H)-one by a method similar to that described in Step 5 of Example 1.

¹H NMR (CDCl₃): δ 8.85 (1H, s), 8.50 (1H, d, J=5.6 Hz), 8.15 (1H, d, J=8.4 Hz), 7.79 (1H, d, J=6.0 Hz), 7.42 (1H, s), 7.24 (1H, dd, J=2.0 Hz, 8.4 Hz), 7.15 (1H, d, J=2.0 Hz), 6.69 (1H, s), 3.98 (3H, s), 3.44 (3H, s) 3.30 (2H, t, J=6.8 Hz), 2.90 (3H, s), 2.58 (2H, t, J=7.2 Hz), 2.28 (6H, s).

Step 6: 1-(2-(5-amino-4-((2-(dimethylamino)ethyl)(methyl)amino)-2-methoxyphenylamino)pyrimidin-4-yl)-5-bromo-3-methyl-1H-benzo[d]imidazol-2(3H)-one

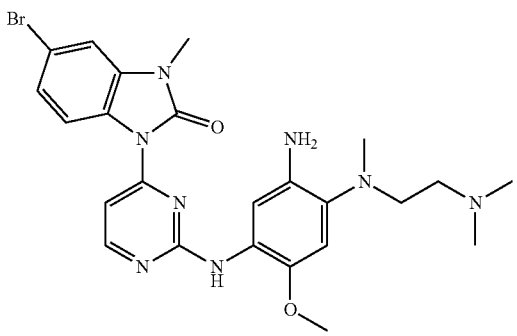

5-Bromo-1-(2-(4-((2-(dimethylamino)ethyl)(methyl)amino)-2-methoxy-5-nitrophenylamino)pyrimidin-4-yl)-3-methyl-1H-benzo[d]imidazol-2(3H)-one (1.00 g) and zinc powder (1.24 g, 18.97 mmol) were dispersed in a mixed solution of dichloromethane/methanol (15 mL/15 mL). 20 mL of saturated ammonium chloride solution was added dropwise at room temperature, and the resulting mixture was stirred for 10 minutes and then filtered. To the filtrate was added water (30 mL) and the resulting mixture was extracted with dichloromethane (30 mL*3). The resulting organic phase was washed with saturated brine and concentrated under vacuum to remove the solvent to give the title compound, which was directly used in the next reaction step.

Step 7: N-(5-(4-(5-bromo-3-methyl-2-oxo-2,3-dihydro-1H-benzo[d]imidazole-1-yl)pyrimidin-2-ylamino)-2-((2-(dimethylamino)ethyl)(methyl)amino)-4-methoxyphenyl) acrylamide Hydrochloride

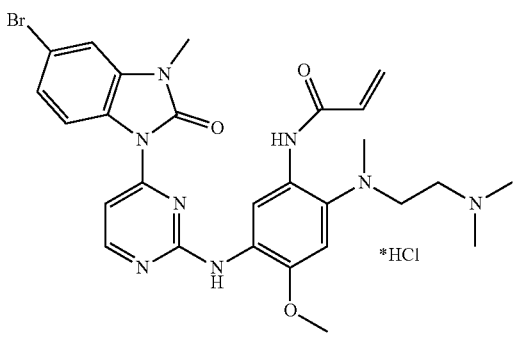 [SMILES: C=CC(=O)Nc1cc(Nc2nccc(-n3c(=O)n(C)c4cc(Br)ccc43)n2)c(OC)cc1N(C)CCN(C)C]

The title compound was prepared from 1-(2-(5-amino-4-((2-(dimethylamino)ethyl) (methyl)amino)-2-methoxyphenylamino)pyrimidin-4-yl)-5-bromo-3-methyl-1H-benzo[d]imidazol-2(3H)-one by a method similar to that described in Step 7 of Example 1.

$^1$H NMR (DMSO-$d_6$): δ 10.23 (1H, br s), 9.82 (1H, br s), 8.75 (1H, s), 8.44 (1H, d, J=5.2 Hz), 8.20 (1H, s), 8.05 (1H, s), 7.65 (1H, d, J=5.2 Hz), 7.49 (1H, d, J=2.0 Hz), 7.08 (1H, d, J=8.4 Hz), 7.00-6.96 (2H, m), 6.21 (1H, dd, J=2.0 Hz, 17.2 Hz), 5.71 (1H, dd, J=1.6 Hz, 10.4 Hz), 3.80 (3H, s), 3.36 (3H, s), 3.29-3.24 (2H, m), 3.16 (3H, s), 2.76-3.68 (2H, m), 2.65 (6H, s).

In Vitro Activity Test

1. Method of In Vitro Enzymatic Assay

EGFR or EGFR (T790M, L858R) kinase was expressed and purified through an insect cell expression system, or purchased as commercially available products.

A platform for testing the activities of EGFR or EGFR (T790M, L858R) kinase was established based on the Homogeneous Time-Resolved Fluorescence (HTRF) method provided by Cisbio Inc., and was used for determining the activities of compounds. The compounds were diluted at a 10-fold gradient with 100% DMSO with a starting concentration of 1 μM. 4 μl of each concentration was taken and added to 96 μl of reaction buffer (50 mM HEPES (pH 7.0), 0.02% NaN$_3$, 0.01% BSA, 0.1 mM Orthovanadate, 5 mM MgCl$_2$, 50 nM SEB, 1 mM DTT). 2.5 μl of the mixture was taken and added to a 384-well plate (OptiPlate-384, PerkinElmer), and then 2.5 μl of the kinase was added. After thoroughly mixing by centrifugation, 5 μl of ATP and TK Substrate-biotin was added to initiate the reaction. The 384-well plate was incubated in an incubator at 23° C. for a period of time, and then the reaction was terminated by adding 5 μl of Eu$^{3+}$-Cryptate labeled TK-Antibody and 5 μl of streptavidin-XL665. The fluorescence values were read on Envision (PerkinElmer) after incubating in the incubator for 1 hour. The IC$_{50}$ values of the compounds were calculated using the GraphPad Prism 5.0 software.

2. Cell Proliferation Assay

Human non-small cell lung cancer cells NCI-H1975 were cultured in RPIM-1640 culture medium supplemented with 10% fetal bovine serum and 1% penicillin-plus-streptomycin in a cell incubator (37° C., 5% CO$_2$). The cells were seeded in a 96-well plate at a density of 2,000 cells per well (volume: 195 μl) and cultured overnight. On the next day, the compounds were added. In particular, the compounds were diluted at a 3-fold gradient with a starting concentration of 10 mM. 4 μl of each concentration was taken and added into 96 μl of culture medium. Then, 5 μl of the mixture was taken and added to a cell culture medium (final DMSO concentration being 0.1%, v/v). After treatment for 72 hours, the medium was aspirated and 30 μl of CellTiter-Glo® (Promega) reagent was added. Fluorescence signals were read on Envison (Perkin Elmer), and IC$_{50}$ values of the compounds for inhibiting cell proliferation were calculated using GraphPad Prism 5.0.

Human skin squamous carcinoma cell line A431 was cultured in DMEM supplemented with 10% fetal bovine serum and 1% penicillin-plus-streptomycin in a cell incubator (37° C., 5% CO$_2$). In the tests of the compounds, the bottom substrate was at a concentration of 0.6%. Cells were re-suspended with 0.3% low-melting-point agar, and then seeded in a 96-well plate at a density of 2,000 cells per well (100 μl). The compounds were diluted at a 3-fold gradient with a starting concentration of 10 mM. 2 μl of each concentration was taken and added to 98 μl of culture medium, and then 5.3 μl of the mixture was added to the cell culture medium (final DMSO concentration being 0.1%, v/v). After treatment for one week (7 days), 20 μl of CellTiter-Blue® (Promega) reagent was added, and the plate was incubated at 37° C. for 4 hours. Fluorescence signals were read on Envison (Perkin Elmer), and IC$_{50}$ values of the compound for inhibiting cell proliferation were calculated using GraphPad Prism 5.0.

TABLE 1

| | Biological activity | | | | |
|---|---|---|---|---|---|
| | Enzymatic activity ($IC_{50}$ nM) | | | Cell viability ($IC_{50}$ nM) | |
| Compound | EGFR(WT) | EGFR-L858R/ T790M(DM) | WT/ DM | A431 | NCI-H1975 |
| AZD9291 | 19.45 | 2.04 | 9.5 | 53.54 | 9.08 |
| Example 1 | 9.07 | 0.72 | 12.6 | 22.49 | 2.76 |
| Example 2 | 2.59 | 0.43 | 6.0 | NT | 0.96 |
| Example 3 | 196.5 | 4.61 | 42.6 | NT | NT |
| Example 4 | 20.61 | 1.15 | 17.9 | NT | 2.87 |
| Example 5 | 44.86 | 2.27 | 19.8 | NT | 16.99 |
| Example 7 | 163.6 | 4.12 | 39.7 | NT | NT |
| Example 9 | 3.93 | 0.64 | 6.1 | NT | NT |
| Example 10 | 10.66 | 0.58 | 18.4 | NT | 1.46 |
| Example 11 | 2.79 | 0.67 | 4.2 | NT | 3.70 |
| Example 12 | 5.26 | 0.50 | 10.5 | NT | 3.17 |
| Example 14 | NT | NT | NT | 537.7 | 4.56 |
| Example 15 | NT | NT | NT | 833.8 | 6.83 |

NT: not tested; AZD9291 was prepared according to the description in Example 28 in WO2013014448.

As can be seen from the above experimental results, in terms of enzymatic activity, the compounds of the present application showed good inhibitory effect on EGFR, especially the EGFR-L858R/T790M double mutant. The WT/DM data showed that the compounds of the present application had desired selectivity. Regarding the experimental results of cell viability, the compounds of the present application showed good inhibitory effect on human non-small cell lung cancer NCI-H1975 and human skin squamous carcinoma cell line A431.

Pharmacokinetic Assay

Healthy adult male rats were subjected to single-dose intragastric administration of the test compounds at a dose of 10 mg/kg with 20% sulfobutyl ether-β-cyclodextrin as an excipient. Before the experiment, the animals were fasted overnight, and the fasting time last from 10 hrs prior to the administration to 4 hrs after the administration. At 0.25, 0.5, 1, 2, 4, 6, 8 and 24 hrs after the intragastric administration, blood sampling was conducted. Approximately 0.3 mL of whole blood was collected from retro-orbital venous sinus, and placed into tubes that contained heparin as an anticoagulant. The samples were centrifuged at 4° C. and 4000 rpm for 5 min. The plasma was transferred into centrifuge tubes, and stored at −80° C. till being analyzed. Concentrations of test compounds in the plasma samples were analyzed with non-validated liquid chromatography-tandem mass spectrometry (LC-MS/MS). Plasma concentration-time data of individual animals was analyzed using Win-Nonlin (Professional Edition, version 6.3; Pharsight Company) software. Non-compartmental model was introduced in concentration analysis. The pharmacokinetic parameters of the test compounds were calculated.

TABLE 2

| | | PO 10 mg/kg | |
|---|---|---|---|
| Parameter | Unit | Compound of Example 13 | Compound of Example 1 |
| $t_{1/2}$ | hr | 2.45 | 1.12 |
| $T_{max}$ | hr | 0.67 | 0.67 |
| $C_{max}$ | ng/mL | 94.4 | 272 |
| $AUC_{0-INF}$ | hr*ng/mL | 401 | 667 |

What is claimed is:

1. A method for inhibiting epidermal growth factor receptor activity in a subject, comprising administering to a subject in need thereof a compound of the formula:

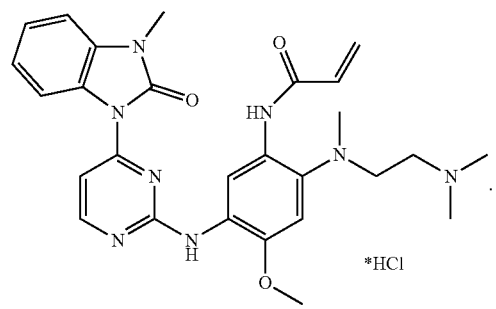 [SMILES: C=CC(=O)Nc1cc(Nc2nccc(-n3c(=O)n(C)c4ccccc43)n2)c(OC)cc1N(C)CCN(C)C]

2. The method according to claim 1, wherein the subject has an epidermal growth factor receptor-mediated disease.

3. The method according to claim 2, wherein the epidermal growth factor receptor-mediated disease is selected from the group consisting of a disease mediated by an epidermal growth factor receptor-L858R activating mutation, a disease mediated by an epidermal growth factor receptor-T790M activating mutation, and a disease mediated by epidermal growth factor receptor-L858R+epidermal growth factor receptor-T790M double-activating mutations.

4. The method according to claim 2, wherein the epidermal growth factor receptor-mediated disease is cancer.

5. The method according to claim 4, wherein the cancer is selected from the group consisting of ovarian cancer, cervical cancer, colorectal cancer, breast cancer, pancreatic cancer, glioma, glioblastoma, melanoma, prostate cancer, leukemia, lymphoma, non-Hodgkin's lymphoma, stomach cancer, lung cancer, hepatocellular cancer, stomach cancer, gastrointestinal stromal tumor, thyroid cancer, cholangiocarcinoma, endometrial cancer, kidney cancer, anaplastic large cell lymphoma, acute myeloid leukemia, multiple myeloma, melanoma, and mesothelioma.

6. The method according to claim 5, wherein the lung cancer is non-small cell lung cancer.

7. A method for treating non-small cell lung cancer in a subject, comprising administering to a subject in need thereof a compound of the formula:

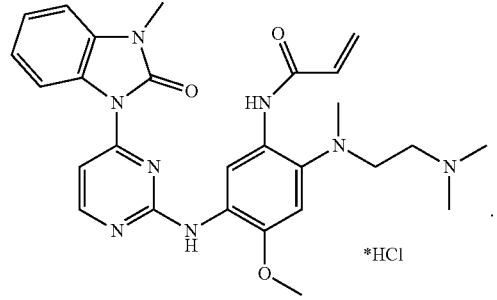 [SMILES: C=CC(=O)Nc1cc(Nc2nccc(-n3c(=O)n(C)c4ccccc43)n2)c(OC)cc1N(C)CCN(C)C]

* * * * *